US008163916B2

(12) United States Patent
Schrimpf et al.

(10) Patent No.: US 8,163,916 B2
(45) Date of Patent: Apr. 24, 2012

(54) AZAADAMANTANE ESTER AND CARBAMATE DERIVATIVES AND METHODS OF USE THEREOF

(75) Inventors: Michael R. Schrimpf, Grayslake, IL (US); Diana L. Nersesian, Gurnee, IL (US); Kevin B. Sippy, Antioch, IL (US); Jianguo Ji, Libertyville, IL (US); Tao Li, Grayslake, IL (US); Lei Shi, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 1040 days.

(21) Appl. No.: 12/052,036

(22) Filed: Mar. 20, 2008

(65) Prior Publication Data

US 2008/0255178 A1    Oct. 16, 2008

Related U.S. Application Data

(60) Provisional application No. 60/896,745, filed on Mar. 23, 2007.

(51) Int. Cl.
C07D 221/22    (2006.01)
(52) U.S. Cl. ....................................... 546/97
(58) Field of Classification Search ........................ None
See application file for complete search history.

(56) References Cited

U.S. PATENT DOCUMENTS

| 4,816,453 | A |   | 3/1989  | Watts |   |
|-----------|---|---|---------|-------|---|
| 5,260,303 | A |   | 11/1993 | Becker et al. |   |
| 5,280,028 | A |   | 1/1994  | Flynn et al. |   |
| 5,399,562 | A |   | 3/1995  | Becker et al. |   |
| 5,434,151 | A |   | 7/1995  | Cai et al. |   |
| 5,521,193 | A | * | 5/1996  | Flynn et al. | 514/290 |
| 5,591,749 | A |   | 1/1997  | Becker et al. |   |
| 5,604,239 | A |   | 2/1997  | Becker et al. |   |
| 5,643,917 | A | * | 7/1997  | Flynn et al. | 514/290 |
| 6,468,998 | B1 | * | 10/2002 | Kuroita et al. | 514/214.03 |

FOREIGN PATENT DOCUMENTS

| GB | 2193633 | 2/1988 |
| WO | 9215593 | 9/1992 |
| WO | 9400454 | 1/1994 |
| WO | 0181347 | 11/2001 |

OTHER PUBLICATIONS

Rautio et al., Prodrugs: Design and Clinical Applications, 7 Nat. Rev. Drug Dis., 255-70 (2008).*
Richard B. Silverman, The Organic Chemistry of Drug Design & Drug Action; Chapter 2: Drug Discovery, Design, & Development, pp. 5-51, Academic Press (1992).*
Tsuneki, H., et al., Journal of Physiol. 547: 169-179 (2002).
William H. Bunnelle et al., Design of Ligands for the Nicotinic Acetylcholine Receptors: The Quest for Selectivity, Current Topics in Medicinal Chemistry, 2004, pp. 299-334, vol. 4.
European Search Report dated Jul. 9, 2009.
Adams, E., et al., Developmental Brain Research, 139: 175-187 (2002).
Adler, E., et al., Schizophrenia Bulletin, 24(2): 189-202 (1998).
Anderson, J., et al., Journal of Pharm. and Exp. Therap., 324(1): 179-187 (2008).
Balbani, A., et al., Expert. Opin. Ther. Pat., 17(3): 287-297 (2007).
Becker, D., et al., Synthesis: 1080-1082 (1992).
Bitner, R., et al., Neuroscience, 325.6 Abstract (2006).
Broad, L., et al., Drugs of the Future, 32(2): 161-170 (2007).
Bunnelle, W., et al., Expert Opin. Ther. Patents, 13(7): 1003-1021 (2003).
Cordero-Erausquin, M., et al., PNAS, 98(5): 2803-2807 (2001).
Couturier, S., et al., Neuron, 5: 847-856 (1990).
Dajas-Bailador, F., et al., Trends in Pharm. Sciences, 25(6): 317-324 (2004).
Decker, M., et al., Expert Opin. Investig. Drugs, 10(10): 1819-1830 (2001).
De Luca, V., et al., Acta Psychiatrica Scand., 114: 211-215 (2006).
Eliel, E., et al., Stereochemistry of Organic Compounds, John Wiley and Sons Inc., New York, NY, Table of Contents (1994).
Falk, L., et al., Developmental Brain Research, 142: 151-160 (2003).
Flynn, D., et al., Bioorganic & Medicinal Chemistry Letters, 2(12): 1613-1618 (1992).
Fernandez, M., et al., J. Heterocyclic Chem., 26: 307-312 (1989).
Friedman, J., et al., Society of Biol. Psych., 51: 349-357 (2002).
Geerts, H., Current Opinion in Invest. Drugs, 7(1): 60-69 (2006).
Gundisch, D., Expert Opin. Ther. Patents, 15(9): 1221-1239 (2005).
Gurwitz, D., Exp. Opin. Invest. Drugs, 8(6): 747-760 (1999).
Hiebl, J., et al., Tetrahedron Letters, 40: 7935-7938 (1999).
Roche, E., Bioreversible Carriers in Drug Design, Pergamon Press, New York, NY, Table of Contents (1987).
Higuchi, T., et al., Pro-Drugs as Novel Drug Delivery Systems, vol. 14 of A.C.S. Symposium Series Table of Contents (1975).
Hogg, R., et al., Rev. Physiol. Biochem. Pharmacol., 147: 1-46 (2003).
Iriepa, I., et al., Journal of Molecular Structure, 509: 105-114 (1999).
Jonnala, R., et al., Journal of Neuroscience Research, 66: 565-572 (2001).
Keller, J., et al., Behav. Brain Research, 162: 143-152 (2005).
Kihara, T., et al., Journal of Biological Chemistry, 276: 13541-13546 (2001).
Leonard, S., et al., European Journal of Pharmacology, 393: 237-242 (2000).
Levin, E., J. Neurobiol., 53: 633-640 (2002).
Liu, Q., et al., PNAS, 98: 4734-4739 (2001).
Pabreza, L., et al., Molecular Pharmacology, 39: 9-12 (1990).
Paterson, D., et al., Progress in Neurobiology, 61: 75-111 (2000).
Prescott, D., Methods in Cell Biology, XIV: 33 et., Academic Press, New York, NY (1996).
Radek, R., et al., Psychopharmacology, 187: 47-55 (2006).
Rowley, M., et al., Journal of Medicinal Chemistry, 44(4): 477-501 (2001).
Sawa, A., et al., Molecular Medicine, pp. 3-9 (2003).

*Primary Examiner* — Janet Andres
*Assistant Examiner* — Timothy R Rozof
(74) *Attorney, Agent, or Firm* — Lisa V. Mueller; Michael, Best & Friedrich LLP

(57) ABSTRACT

The invention relates to compounds that are substituted azaadamantane ester and carbamate derivatives, compositions comprising such compounds, and methods of using such compounds and compositions.

12 Claims, No Drawings

OTHER PUBLICATIONS

Shimohama, S., et al., Brain Research, 779: 359-363 (1988).
Stevens, K., Psychopharmacology, 136: 320-327 (1998).
Stotter, P., et al., Heterocycles, 25: 251-258 (1987).
Vincler, M., Expert Opin. Investig. Drugs, 14(10): 1191-1198 (2005).
Vincler, M., et al., Expert Opin. Ther. Targets, 11(7): 891-897 (2007).
Wilens, T., et al., Biol. Psychiatry, 59(11): 1065-1070 (2006).
Wilens, Timothy e. et al., Am J Psychiatry, 156(12): 1931-1937 (1999).
Korolkoras, A., Essentials of Medicinal Chemistry, John Wiley-Interscience Publications, John Wiley & Sons, New York, 97-118 (1988).
Greene, T. W., et al., Protecting Groups in Chemical Synthesis (3rd ed), John Wiley & Sons, NY, Table of Contents (1999).
PCT International Search Report, PCT/US2008/057641, mailing date Aug. 13, 2008.
Izquierdo, M., et al., Journal of Mol. Structure, 213: 175-183 (1989).
Galvez, A., et al., Journal of Heterocyclic Chem., 26(2): 349-353 (1989).
Delpech, B., et al., Journal of Organic Chem., 43(25): 4898-4900 (1978).
Alkondon, M., et al., Prog. Brain Res. 145: 109-120 (2004).
Gotti, C., et al., Prog. Neurobiol., 74: 363-396 (2004).
Tsuneki, H., et al., J. Physiol., 547: 169-179 (2003).

* cited by examiner

AZAADAMANTANE ESTER AND CARBAMATE DERIVATIVES AND METHODS OF USE THEREOF

This application claims priority from U.S. Provisional Patent Application Ser. No. 60/896,745 filed Mar. 23, 2007, which is hereby incorporated by reference in entirety.

BACKGROUND OF THE INVENTION

1. Technical Field

The invention relates to azaadamantane ester and carbamate derivatives, compositions comprising such compounds, and methods of preventing or treating conditions and disorders using such compounds and compositions.

2. Description of Related Technology

Nicotinic acetylcholine receptors (nAChRs), belonging to the super family of ligand gated ion channels (LGIC), are widely distributed throughout the central nervous system (CNS) and the peripheral nervous system (PNS), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are understood to play an important role in regulating CNS function and the release of many neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of NNRs exist in the CNS and periphery. Each subtype has a different effect on regulating the overall physiological function.

Typically, NNRs are ion channels that are constructed from a pentameric assembly of subunit proteins. Sixteen subunits of nAChRs have been reported to date, which are identified as $\alpha 2$-$\alpha 10$, $\beta 1$-$\beta 4$, $\gamma$, $\delta$, and $\epsilon$. Of these subunits, nine subunits, $\alpha 2$ through $\alpha 7$ and $\beta_2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in the case of $\alpha 4\beta 2$ and $\alpha 3\beta 4$ receptors (see for example, Vincler, M., McIntosh, J. M., Targeting the $\alpha 9\alpha 10$ nicotinic acetylcholine receptor to treat severe pain, *Exp. Opin. Ther. Targets*, 2007, 11 (7): 891-897; Paterson, D. and Nordberg, A., Neuronal nicotinic receptors in the human brain, *Prog. Neurobiol.* 2000, 61: 75-111; Hogg, R. C., Raggenbass, M., Bertrand, D., Nicotinic acetylcholine receptors: from structure to brain function, *Rev. Physiol., Biochem. Pharmacol.*, 2003, 147: 1-46; Gotti, C., Clementi, F., Neuronal nicotinic receptors: from structure to pathology, *Prog. Neurobiol.*, 2004, 74: 363-396). These subunits provide for a great variety of homomeric and heteromeric combinations that account for the diverse receptor subtypes.

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence (see for example, Keller, J. J., Keller, A. B., Bowers, B. J., Wehner, J. M., Performance of alpha7 nicotinic receptor null mutants is impaired in appetitive learning measured in a signaled nose poke task, *Behav. Brain Res.*, 2005, 162: 143-52; Gundish, D., Nicotinic acetylcholine receptor ligands as potential therapeutics, *Expert Opin. Ther. Patents*, 2005, 15 (9): 1221-1239; De Luca, V., Likhodi, O., Van Tol, H. H., Kennedy, J. L., Wong, A. H., Regulation of alpha7-nicotinic receptor subunit and alpha7-like gene expression in the prefrontal cortex of patients with bipolar disorder and schizophrenia, *Acta Psychiatr. Scand.*, 2006, 114: 211-5).

The homomeric $\alpha 7$ receptor is one of the most abundant nicotinic receptors, along with $\alpha 4\beta 2$ receptors, in the human brain, wherein it is heavily expressed in the hippocampus, cortex, thalamic nuclei, ventral tegmental area and substantia nigra (see for example, Broad, L. M., Sher, E., Astles, P. C., Zwart, R., O'Neill, M. J., Selective $\alpha 7$ nicotinic acetylcholine receptor ligands for the treatment of neuropsychiatric diseases, *Drugs of the Future*, 2007, 32(2): 161-170).

The role of $\alpha 7$ NNRs in neuronal signaling in the CNS also has been actively investigated (see for example, Couturier, S., Bertrand, D., Matter, J. M., Hernandez, M. C., Bertrand, S., Millar, N., Valera, S., Barkas, T., Ballivet, M., A neuronal nicotinic acetylcholine receptor subunit (alpha 7) is developmentally regulated and forms a homo-oligomeric channel blocked by alpha-BTX, *Neuron*, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., Albuquerque, E. X., The nicotinic acetylcholine receptor subtypes and their function in the hippocampus and cerebral cortex, *Prog. Brain Res.*, 2004, 145: 109-20).

Biophysical studies have shown that ion channels comprised of $\alpha 7$ subunits, when expressed in heterologous expression systems, activate and desensitize rapidly, and furthermore, exhibit relatively higher calcium permeability compared to other NNR combinations (see for example, Dajas-Bailador, F., Wonnacott, S., Nicotinic acetylcholine receptors and the regulation of neuronal signaling, *Trends Pharmacol. Sci.*, 2004, 25: 317-24).

The NNR ligands have been also implicated in smoking cessation, weight control and as potential analgesics (see for example, Balbani, A. P. S., Montovani, J. C., Recent developments for smoking cessation and treatment of nicotine dependence, *Exp. Opin. Ther. Patents*, 2003, 13 (7): 287-297; Gurwitz, D., The therapeutic potential of nicotine and nicotinic agonists for weight control, *Exp. Opin. Invest. Drugs*, 1999, 8(6): 747-760; Vincler, M., Neuronal nicotinic receptors as targets for novel analgesics, *Exp. Opin. Invest. Drugs*, 2005, 14 (10): 1191-1198; Bunnelle, W. H., Decker, M. W., Neuronal nicotinic acetylcholine receptor ligands as potential analgesics, *Exp. Opin. Ther. Patents*, 2003, 13 (7): 1003-1021; Decker, M. W., Meyer, M. D., Sullivan, J. P., The therapeutic potential of nicotinic acetylcholine receptor agonists for pain control, *Exp. Opin. Invest. Drugs*, 2001, 10(10): 1819-1830; Vincler, M., McIntosh, J. M., Targeting the $\alpha_9\alpha_{10}$ nicotinic acetylcholine receptor to treat severe pain, *Exp. Opin. Ther. Targets*, 2007, 11 (7): 891-897).

The $\alpha 7$ and $\alpha 4\beta 2$ NNRs have been shown to play a significant role in enhancing cognitive function, including aspects of learning, memory and attention (Levin, E. D., J. Neurobiol. 53: 633-640, 2002). For example, $\alpha 7$ NNRs have been linked to conditions and disorders related to attention deficit disorder, ADHD, AD, mild cognitive impairment, senile dementia, dementia associated with Lewy bodies, dementia associated with Down's syndrome, AIDS dementia, Pick's disease, as well as cognitive deficits associated with schizophrenia (CDS), among other systemic activities. The $\alpha 4\beta 2$ receptor subtype is implicated in attention, cognition, epilepsy, and pain control (Paterson, D. and Nordberg, A., Neuronal nicotinic receptors in the human brain, *Prog. Neurobiol.* 2000, 61: 75-111).

Certain compounds, like the plant alkaloid nicotine, interact with all known subtypes of the nAChRs, accounting for the profound physiological effects of this compound. Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems that interfere at therapeutic doses, and its addictive nature and acute toxicity are well-known. Accordingly, there is a need to identify subtype-selective compounds that evoke the beneficial effects of nicotine while eliminating or decreasing adverse effects.

The activity at the NNRs can be modified or regulated by the administration of subtype selective NNR ligands. The ligands can exhibit antagonist, agonist, or partial agonist properties and thus have potential in treatment of various cognitive disorders.

Although compounds that nonselectively demonstrate activity at a range of nicotinic receptor subtypes including the α4β2 and α7 NNRs are known, it would be beneficial to provide compounds that interact selectively with α7-containing neuronal NNRs, α4β2 NNRs, or both α7 and α4β2 NNRs compared to other subtypes.

SUMMARY OF THE INVENTION

The invention is directed to ester and carbamate derivatives of azaadamantane containing compounds as well as compositions comprising such compounds, and methods of using the same.

One aspect of the invention relates to compounds of formula (I)

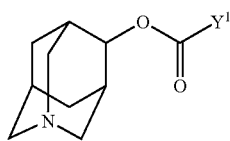

(I)

wherein
$Y^1$ is A, —N($R^X$)-A, or —C($R^Y$)=C($R^Z$)-A; with the proviso that $Y^1$ is other than unsubstituted benzothien-3-yl or 4-chlorophenyl;

A is aryl, heteroaryl, heterocycle, arylalkyl, heteroarylalkyl, or heterocyclealkyl; and $R^X$, $R^Y$, and $R^Z$, at each occurrence, are each independently hydrogen, alkyl, or haloalkyl;

or a pharmaceutically acceptable salt, amide, ester or prodrug thereof.

Another aspect of the invention relates to pharmaceutical compositions comprising compounds of the invention. Such compositions can be administered in accordance with a method of the invention, typically as part of a therapeutic regimen for treatment or prevention of conditions and disorders related to NNR activity, and more particularly α7 NNR activity, α4β2 NNR activity, or both α7 NNR activity and α4β2 NNR activity.

A further aspect of the invention relates to a method of modulating α7 NNR activity, α4β2 NNR activity, or both α7 NNR activity and α4β2 NNR activity. The method is useful for treating, preventing, or both treating and preventing conditions and disorders related to α7 NNR activity, α4β2 NNR activity, or both α7 NNR activity and α4β2 NNR activity in mammals. More particularly, the method is useful for conditions and disorders related to attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, smoking cessation, ischemia, sepsis, wound healing, and other complications associated with diabetes, among other systemic and neuroimmunomodulatory activities.

The compounds, compositions comprising the compounds, and methods for treating or preventing conditions and disorders by administering the compounds are further described herein.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms, including, but not limited to, lower alkyl, $C_{1-6}$ alkyl and $C_{1-3}$ alkyl. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl, a bicyclic aryl, or a tricyclic aryl. The bicyclic aryl is naphthyl, or a phenyl fused to a monocyclic cycloalkyl, or a phenyl fused to a monocyclic cycloalkenyl. Representative examples of the bicyclic aryls include, but are not limited to, dihydroindenyl, indenyl, naphthyl, dihydronaphthalenyl, and tetrahydronaphthalenyl. The tricyclic aryl is a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, and tetrahydrophenanthrenyl. The aryl groups of the present invention can be unsubstituted or substituted and are attached to the parent molecular moiety through any carbon atom contained within the ring systems.

The term "arylalkyl" as used herein, means an aryl group, as defined herein, appended to the parent molecular moiety through an alkyl group, as defined herein. Representative examples of arylalkyl include, but are not limited to, benzyl (phenylmethyl), 2-phenylethyl, and 3-phenylpropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, and a tricyclic cycloalkyl. The monocyclic cycloalkyl is a monocyclic carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge of one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, andbicyclo[4.2.1]nonane. Tricyclic cycloalkyls are exemplified by a bicyclic cycloalkyl fused to a monocyclic cycloalkyl, or a bridged bicyclic cycloalkyl in which two non-adjacent carbon atoms of the bicyclic ring system are linked by an alkylene bridge of between one and four carbon atoms. Representative examples of tricyclic-ring systems include, but are not limited to, octahydro-2,5-methanopentalene (tricyclo[3.3.1.0$^{3,7}$]nonane or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring systems.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, and cyclohexylmethyl.

The term "cycloalkenyl" or "cycloalkene" as used herein, means a monocyclic or a bicyclic hydrocarbon ring system. The monocyclic cycloalkenyl has four, five, six, seven or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms and each linking two non-adjacent carbon atoms of the ring. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted, and are attached to the parent molecular moiety through any substitutable atom contained within the ring systems.

The term "cycloalkenylalkyl" as used herein, means a cycloalkenyl group, as defined herein, appended to the parent molecular moiety through an alkyl group, as defined herein.

The term "ethylenedioxy" as used herein, means a —O—(CH$_2$)$_2$—O— group wherein the oxygen atoms of the ethylenedioxy group are attached to two adjacent carbon atoms of a phenyl or naphthyl moiety, forming a six membered ring with the two adjacent carbon atoms of the phenyl or naphthyl moiety that it is attached to.

The term "halo" or "halogen" as used herein, means Cl, Br, I, or F.

The term "haloalkyl" as used herein, means an alkyl group, as defined herein, in which one, two, three, four, five, or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or four nitrogen atoms; or one, two, or three nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, thieno[2,3-c]pyridinyl, and 5,6,7,8-tetrahydroquinolin-5-yl. The monocyclic and bicyclic heteroaryl groups of the present invention can be substituted or unsubstituted, and are connected to the parent molecular moiety through any substitutable carbon atom or any substitutable nitrogen atom contained within the ring systems.

The term "heteroarylalkyl" as used herein, means a heteroaryl, as defined herein, appended to the parent molecular moiety through an alkyl group, as defined herein.

The term "heteroatom" as used herein, means a nitrogen, oxygen, or sulfur atom.

The term "heterocycle" or "heterocyclic" as used herein, means a monocyclic, a bicyclic, or a tricyclic heterocycle ring system, provided that the heterocycle is not 1,3-benzodioxolyl, 2,3-dihydro-1,4-benzodioxine, naphtho[2,3-d][1,3]dioxole, or 2,3-dihydronaphtho[2,3-b][1,4]dioxine. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven-membered ring contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, tetrahydropyranyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, and 2,3-dihydro-1 H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bridged bicyclic heterocycle in which two non adjacent atoms of the bicyclic ring are linked by an alkylene bridge consisting of one, two, three, or four carbon atoms. An example of a tricyclic heterocycle is azaadmantane such as 1-azatricyclo[3.3.1.1$^{3,7}$]decane. The monocyclic, bicyclic and tricyclic heterocycles are connected to the parent molecular moiety through any substitutable carbon or nitrogen atom contained within the ring systems, and can be unsubstituted or substituted.

The term "heterocyclealkyl" as used herein, means a heterocycle, as defined herein, appended to the parent molecular moiety through an alkyl group, as defined herein.

The term "methylenedioxy" as used herein, means a —O—(CH$_2$)—O— group wherein the oxygen atoms of the methylenedioxy group are attached to two adjacent carbon atoms of the phenyl or naphthyl ring, forming a five membered ring with the two adjacent carbon atoms of the phenyl or naphthyl moiety that it is attached to.

The term "oxo" as used herein, means a =O group.

The term "parenterally," as used herein, refers to modes of administration, including intravenous, intramuscular, intraperitoneal, intrasternal, subcutaneous, intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "pharmaceutically acceptable salts, esters and amides" as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base functional group with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, malate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The term "tautomer" as used herein means a proton shift from one atom of a compound to another atom of the same compound wherein two or more structurally distinct compounds are in equilibrium with each other.

The terms "unsubstituted or substituted" with reference to aryl, cycloalkyl, cycloalkenyl, heterocycle, or heteroaryl moieties of this invention, as a substituent, or as part of a substituent, each independently, as used herein mean unsubstituted or substituted with 1, 2, 3, 4, or 5 substituents as described hereinbelow, unless otherwise noted. The optional substituents are selected from the group consisting of alkyl, alkenyl, alkynyl, halogen, cyano, oxo, methylenedioxy, ethylenedioxy, -$G^1$, —$NO_2$, —$OR^{1a}$, —$OC(O)R^{1a}$, —$OC(O)N(R^b)(R^a)$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^a$, —$N(R^a)C(O)O(R^{1a})$, —$N(R^a)C(O)N(R^b)(R^a)$, —$(CR^{4a}R^a)_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^a)$, —$(CR^{4a}R^{5a})_m$—$SR^{1a}$, —$(CR^{4a}R^{5a})_m S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^a)$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, cyanoalkyl, and haloalkyl; wherein $R^{1a}$ and $R^{3a}$, at each occurrence, are each independently hydrogen, alkyl, haloalkyl, $G^1$, or —$(CR^6R^7)_n$-$G^1$;

$R^{2a}$, at each occurrence, is independently alkyl, haloalkyl, $G^1$, or —$(CR^6R^7)_n$-$G^1$;

$R^{4a}$, $R^{5a}$, $R^6$, and $R^7$, at each occurrence, are each independently hydrogen, halogen, alkyl, or haloalkyl;

$R^a$ and $R^b$, at each occurrence, are each independently hydrogen, alkyl, or haloalkyl;

m and n, at each occurrence, are each independently 1, 2, 3, 4, or 5;

$G^1$ is aryl, heteroaryl, heterocycle, cycloalkyl, or cycloalkenyl, wherein each $G^1$ is independently unsubstituted or substituted with 1, 2, 3, 4 or 5 substituents selected from the group consisting of alkyl, alkenyl, alkynyl, halogen, cyano, oxo, methylenedioxy, ethylenedioxy, —$NO_2$, —$OR^{1b}$, —$OC(O)R^{1b}$, —$OC(O)N(R^b)(R^{3b})$, —$SR^{1b}$, —$S(O)_2R^{2b}$, —$S(O)_2N(R^b)(R^{3b})$, —$C(O)R^{1b}$, —$C(O)OR^{1b}$, $C(O)N(R^b)(R^{3b})$, —$N(R^b)(R^{3b})$, —$N(R^a)C(O)R^{1b}$, —$N(R^a)S(O)_2R^{2b}$, —$N(R^a)C(O)O(R^{1b})$, —$N(R^a)C(O)N(R^b)(R^{3b})$, —$(CR^{4b}R^{5b})_m$—$NO_2$, —$(CR^{4b}R^{5b})_m OR^{1b}$, —$(CR^{4b}R^{5b})_m OC(O)R^{1b}$, —$(CR^{4b}R^{5b})_m OC(O)N(R^b)(R^{3b})$, —$(CR^{4b}R^{5b})_m$—$SR^{1b}$, —$(CR^{4b}R^{5b})_m S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m C(O)OR^{1b}$, $(CR^{4b}R^{5b})_m C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)S(O)_2R^{2b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;

$R^{1b}$ and $R^{3b}$, at each occurrence, are each independently hydrogen, alkyl, or haloalkyl;

$R^{2b}$, at each occurrence, is independently alkyl or haloalkyl; and $R^{4b}$ and $R^{5b}$, at each occurrence, are each independently hydrogen, halogen, alkyl, or haloalkyl.

Compounds of the Invention

In one aspect, the invention relates to compounds of formula (I), (I)

wherein $Y^1$ is A, —$N(R^X)$-A, or —$C(R^Y)$=$C(R^Z)$-A; with the proviso that $Y^1$ is other than unsubstituted benzothien-3-yl or 4-chlorophenyl;

A is aryl, heteroaryl, heterocycle, arylalkyl, heteroarylalkyl, or heterocyclealkyl; and $R^X$, $R^Y$, and $R^Z$, at each occurrence, are each independently hydrogen, alkyl, or haloalkyl;

or a pharmaceutically acceptable salt, amide, ester or prodrug thereof.

In one embodiment, the invention is a compound of formula I as defined above, wherein A is unsubstituted or substituted aryl or heteroaryl, or a pharmaceutically acceptable salt, amide, ester or prodrug thereof.

Particular examples of one embodiment of the invention include compounds of formula I, wherein the aryl is phenyl or naphthyl, with the proviso that when $Y^1$ is A, then A is other than 4-chlorophenyl, or a pharmaceutically acceptable salt, amide, ester or prodrug thereof.

Specific examples of an embodiment of the invention include compounds of formula I, wherein the heteroaryl is unsubstituted or substituted pyridinyl, pyrimidinyl, pyrazinyl, thienyl, furanyl, pyrrolyl, oxazolyl, thiazolyl, oxathiazolyl, isoxazolyl, isothiazolyl, pyrazolyl, imidazolyl, benzothienyl, benzofuranyl, benzimidazolyl, indolyl, indazolyl, thieno[2,3-c]pyridinyl, quinolinyl, and isoquinolinyl, with the proviso that when $Y^1$ is A, then A is other than unsubstituted benzothien-3-yl, or a pharmaceutically acceptable salt, amide, ester or prodrug thereof.

In a preferred embodiment of the invention, $Y^1$ in formula (I) is bicyclic aryl or bicyclic heteroaryl, or a pharmaceutically acceptable salt, amide, ester or prodrug thereof. Specific examples of bicyclic aryl and bicyclic heteroaryl include, but are not limited to, naphthyl, indole, benzothiophene, and benzofuran.

Another embodiment of the invention is a compound of formula I, wherein A is unsubstituted or substituted heterocycle. Preferred examples of this embodiment include compounds of formula I, wherein A is unsubstituted or substituted 2,3-dihydrobenzofuranyl or 2,3-dihydrobenzothienyl, or a pharmaceutically acceptable salt, amide, ester or prodrug thereof.

Yet another embodiment of the invention is a compound of formula I, wherein A is unsubstituted or substituted arylalkyl or heteroarylalkyl, or a pharmaceutically acceptable salt, amide, ester or prodrug thereof. One particular example of this embodiment is a compound of formula I, wherein A is benzyl.

One embodiment of the invention is a compound of formula I, wherein $Y^1$ is A, or a pharmaceutically acceptable salt, amide, ester or prodrug thereof.

Another embodiment of the invention is a compound of formula I, wherein $Y^1$ is —$N(R^X)$-A, or a pharmaceutically acceptable salt, amide, ester or prodrug thereof.

In another embodiment, the invention is a compound of formula I, wherein $Y^1$ is —C($R^Y$)=C($R^Z$)-A, or a pharmaceutically acceptable salt, amide, ester or prodrug thereof.

In various embodiments of the invention, particular examples of the optional substituents of A include unsubstituted or substituted alkyl, aryl, haloalkyl, heteroaryl, haloalkyl, halogen and hydroxyl. Preferred examples of alkyl include, but are not limited to, methyl, ethyl and propyl. Preferred examples of haloalkyl include, but are not limited to, trifluoromethyl or difluoromethyl. A preferred example of haloalkyl is trifluoromethyl.

Particular examples of aryl and heteroaryl as optional substituents of A include, but are not limited to, unsubstituted or substituted phenyl, naphthyl, pyridinyl, pyrimidinyl, pyrazinyl, thienyl, furanyl, pyrrolyl, oxazolyl, thiazolyl, oxathiazolyl, isoxazolyl, isothiazolyl, pyrazolyl, imidazolyl, benzothienyl, benzofuranyl, benzimidazolyl, indolyl, indazolyl, thieno[2,3-c]pyridinyl, quinolinyl, isoquinolinyl, 2,3-dihydrobenzofuranyl, 2,3-dihydrobenzothienyl, and hexahydropyrrolo[3,4-c]pyrrol-2(1 H)-yl.

Exemplary compounds of various embodiments of the invention include, but are not limited to:

(4s)-(6-chloronicotinoyloxy)-1-azatricyclo[3.3.1.1$^{3,7}$]decane;
(4r)-(6-chloronicotinoyloxy)-1-azatricyclo[3.3.1.1$^{3,7}$]decane;
(4r)-(6-phenylnicotinoyloxy)-1-azatricyclo[3.3.1.1$^{3,7}$]decane;
(4s)-[6-(indol-5-yl)nicotinoyloxy]-1-azatricyclo[3.3.1.1$^{3,7}$]decane;
(4r)-[6-(indol-5-yl)nicotinoyloxy]-1-azatricyclo[3.3.1.1$^{3,7}$]decane;
(4s)-(5-bromonicotinoyloxy)-1-azatricyclo[3.3.1.1$^{3,7}$]decane;
(4r)-(5-bromonicotinoyloxy)-1-azatricyclo[3.3.1.1$^{3,7}$]decane;
(4r)-(5-phenylnicotinoyloxy)-1-azatricyclo[3.3.1.1$^{3,7}$]decane;
(4s)-[5-(indol-5-yl)nicotinoyloxy]-1-azatricyclo[3.3.1.1$^{3,7}$]decane;
(4r)-[5-(indol-5-yl)nicotinoyloxy]-1-azatricyclo[3.3.1.1$^{3,7}$]decane;
(4s)-(furan-2-oyloxy)-1-azatricyclo[3.3.1.1$^{3,7}$]decane;
(4r)-(furan-2-oyloxy)-1-azatricyclo[3.3.1.1$^{3,7}$]decane;
(4s)-(5-bromofuran-2-oyloxy)-1-azatricyclo[3.3.1.1$^{3,7}$]decane;
(4r)-(5-bromofuran-2-oyloxy)-1-azatricyclo[3.3.1.1$^{3,7}$]decane;
(4s)-(4,5-dimethylfuran-2-oyloxy)-1-azatricyclo[3.3.1.1$^{3,7}$]decane;
(4r)-(4,5-dimethylfuran-2-oyloxy)-1-azatricyclo[3.3.1.1$^{3,7}$]decane;
(4s)-(thiophen-2-oyloxy)-1-azatricyclo[3.3.1.1$^{3,7}$]decane;
(4r)-(thiophen-2-oyloxy)-1-azatricyclo[3.3.1.1$^{3,7}$]decane;
(4s)-(thiophen-3-oyloxy)-1-azatricyclo[3.3.1.1$^{3,7}$]decane;
(4r)-(thiophen-3-oyloxy)-1-azatricyclo[3.3.1.1$^{3,7}$]decane;
(4s)-(5-chlorothiophen-2-oyloxy)-1-azatricyclo[3.3.1.1$^{3,7}$]decane;
(4r)-(5-chlorothiophen-2-oyloxy)-1-azatricyclo[3.3.1.1$^{3,7}$]decane;
(4s)-(5-methylthiophen-2-oyloxy)-1-azatricyclo[3.3.1.1$^{3,7}$]decane;
(4r)-(5-methylthiophen-2-oyloxy)-1-azatricyclo[3.3.1.1$^{3,7}$]decane;
(4s)-(5-bromothiophen-2-oyloxy)-1-azatricyclo[3.3.1.1$^{3,7}$]decane;
(4r)-(5-bromothiophen-2-oyloxy)-1-azatricyclo[3.3.1.1$^{3,7}$]decane;
(4s)-(3-bromothiophen-2-oyloxy)-1-azatricyclo[3.3.1.1$^{3,7}$]decane;
(4r)-(3-bromothiophen-2-oyloxy)-1-azatricyclo[3.3.1.1$^{3,7}$]decane;
(4s)-(5-(2-thienyl)thiophen-2-oyloxy)-1-azatricyclo[3.3.1.1$^{3,7}$]decane;
(4r)-(5-(2-thienyl)thiophen-2-oyloxy)-1-azatricyclo[3.3.1.1$^{3,7}$]decane;
(4s)-1-azatricyclo[3.3.1.1$^{3,7}$]decan-4-yl 2-(thiophen-2-yl)thiazole-4-carboxylate
(4r)-1-azatricyclo[3.3.1.1$^{3,7}$]decan-4-yl 2-(thiophen-2-yl)thiazole-4-carboxylate;
(4s)-(2-naphthoyloxy)-1-azatricyclo[3.3.1.1$^{3,7}$]decane;
(4s)-(benzothiophen-5-oyloxy)-1-azatricyclo[3.3.1.1$^{3,7}$]decane;
(4r)-(benzothiophen-5-oyloxy)-1-azatricyclo[3.3.1.1$^{3,7}$]decane;
(4s)-(thieno[2,3-c]pyridine-5-oyloxy)-1-azatricyclo[3.3.1.1$^{3,7}$]decane;
(4r)-(thieno[2,3-c]pyridine-5-oyloxy)-1-azatricyclo[3.3.1.1$^{3,7}$]decane;
(4s)-(5-bromoindol-3-oyloxy)-1-azatricyclo[3.3.1.1$^{3,7}$]decane;
(4s)-(4-bromoindol-3-oyloxy)-1-azatricyclo[3.3.1.1$^{3,7}$]decane;
(4s)-(indol-3-oyloxy)-1-azatricyclo[3.3.1.1$^{3,7}$]decane;
(4s)-(indol-6-oyloxy)-1-azatricyclo[3.3.1.1$^{3,7}$]decane;
(4s)-(benzofuran-5-oyloxy)-1-azatricyclo[3.3.1.1$^{3,7}$]decane;
(4s)-(5-methoxy-2-methylbenzofuran-3-oyloxy)-1-azatricyclo[3.3.1.1$^{3,7}$]decane;
(4s)-(benzothien-5-ylcarbamoyloxy)-1-azatricyclo[3.3.1.1$^{3,7}$]decane;
(4r)-(benzothien-5-ylcarbamoyloxy)-1-azatricyclo[3.3.1.1$^{3,7}$]decane;
(4s)-(4-bromophenylcarbamoyloxy)-1-azatricyclo[3.3.1.1$^{3,7}$]decane;
(4r)-(4-bromophenylcarbamoyloxy)-1-azatricyclo[3.3.1.1$^{3,7}$]decane;
(4s)-(2-hydroxyphenylcarbamoyloxy)-1-azatricyclo[3.3.1.1$^{3,7}$]decane;
(4s)-(2,3-dihydrobenzofuran-5-ylcarbamoyloxy)-1-azatricyclo[3.3.1.1$^{3,7}$]decane;
(4s)-(benzylcarbamoyloxy)-1-azatricyclo[3.3.1.1$^{3,7}$]decane;
(4r)-(benzylcarbamoyloxy)-1-azatricyclo[3.3.1.1$^{3,7}$]decane;
(4s)-1-azatricyclo[3.3.1.1$^{3,7}$]dec-4-yl 5-(hexahydropyrrolo[3,4-c]pyrrol-2(1 H) -yl)nicotinate;
(4r)-1-azatricyclo[3.3.1.1$^{3,7}$]dec-4-yl 5-(hexahydropyrrolo[3,4-c]pyrrol-2(1 H) -yl)nicotinate;
(4s)-1-azatricyclo[3.3.1.1$^{3,7}$]dec-4-yl 2-bromothiazole-4-carboxylate;
(4s)-1-azatricyclo[3.3.1.1$^{3,7}$]dec-4-yl 5-fluoronicotinate;
(4s)-1-azatricyclo[3.3.1.1$^{3,7}$]dec-4-yl 5-(1 H-pyrrol-1-yl)nicotinate;
(4s)-1-azatricyclo[3.3.1.1$^{3,7}$]dec-4-yl 3,4'-bipyridine-5-carboxylate;
(4s)-1-azatricyclo[3.3.1.1$^{3,7}$]dec-4-yl 5-(4-chlorophenyl)nicotinate;
(4s)-1-azatricyclo[3.3.1.1$^{3,7}$]dec-4-yl 5-(4-(trifluoromethyl)phenyl)nicotinate;
(4r)-1-azatricyclo[3.3.1.1$^{3,7}$]dec-4-yl 5-(pyridin-2-yl)thiophene-2-carboxylate; and
(4s)-1-azatricyclo[3.3.1.1$^{3,7}$]dec-4-yl nicotinate;
or pharmaceutically acceptable salts, amides, esters or prodrugs thereof.

In another embodiment of the invention, the specific examples include, but are not limited to, (4s)-(2-naphthoyloxy)-1-azatricyclo[3.3.1.1$^{3,7}$]decane;
(4s)-(benzothiophen-5-oyloxy)-1-azatricyclo[3.3.1.1$^{3,7}$]decane;
(4s)-(indol-3-oyloxy)-1-azatricyclo[3.3.1.1$^{3,7}$]decane;
(4s)-(indol-6-oyloxy)-1-azatricyclo[3.3.1.1$^{3,7}$]decane;
(4s)-(benzofuran-5-oyloxy)-1-azatricyclo[3.3.1.1$^{3,7}$]decane;

or pharmaceutically acceptable salts, amides, esters or prodrugs thereof.

Compounds disclosed herein may contain asymmetrically substituted carbon or sulfur atoms, and accordingly may exist in, and be isolated as, single stereoisomers (e.g. single enantiomer or single diastereomer), mixtures of stereoisomers (e.g. any mixture of enantiomers or diastereomers) or racemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures of various proportions thereof, which form possesses properties useful in the modulation of NNRs activity, particularly α7NNRs, α4β2, or both α7 and α4β2. Where the stereochemistry of the chiral centers present in the chemical structures illustrated herein is not specified, the chemical structure is intended to encompass compounds containing either stereoisomer of each chiral center, and mixtures thereof.

For example, formula (Ia) and (Ib) represent some of the stereoisomeric forms that compounds of formula (I) possesses:

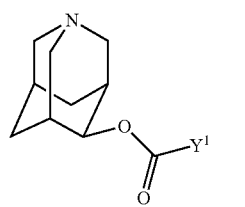
(Ia)

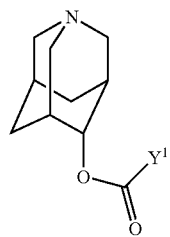
(Ib)

The aza-adamantane portion of isomer (Ia) and isomer (Ib) is not chiral, however the C-4 carbon at which oxygen is attached is considered pseudoasymmetric. Compounds represented by formula (Ia) and (Ib) are diastereomers. The configurational assignment of structures of formula (Ia) are assigned 4r in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Ib) are assigned 4s using the same methods.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycloalkyl group. Substituents around a carbon-carbon double bond or a carbon-nitrogen bond are designated as being of Z or E configuration and substituents around a cycloalkyl or heterocycle are designated as being of cis or trans configuration.

It is to be understood that compounds disclosed herein may exhibit the phenomenon of tautomerism.

The compounds within this specification may be represented by only one of the possible tautomeric, geometric or stereoisomeric forms in the formulae and names. However, it is to be understood that the invention encompasses any possible tautomeric, geometric or stereoisomeric forms, and mixtures thereof, and is not to be limited merely to any one tautomeric, geometric or stereoisomeric form utilized within the naming of the compounds or formulae drawings.

Amides, Esters and Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated herein in its entirety by reference.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

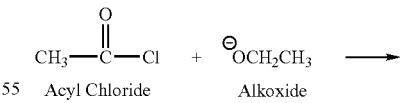
Acyl Chloride    Alkoxide

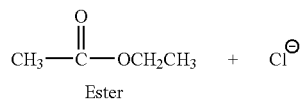
Ester

Amides can be prepared from substrates of formula (I) containing either an amino group or a carboxy group in similar fashion. Esters can also react with amines or ammonia to form amides.

Scheme 2

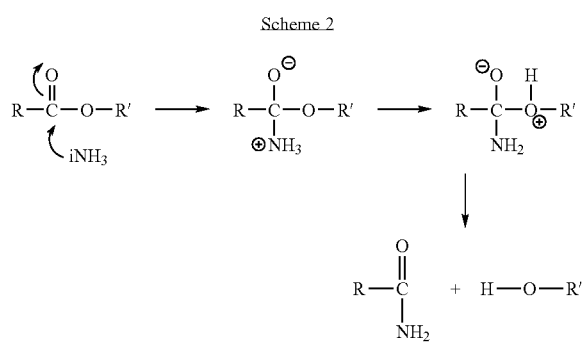

Another way to make amides from compounds of formula (I) is to heat carboxylic acids and amines together.

Scheme 3

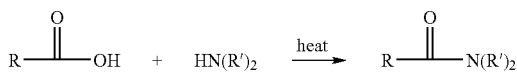

In Schemes 2 and 3, R and R' are independently substrates of formula (I), alkyl or hydrogen. Various embodiments of the invention of formula (I) that are substrates for prodrugs, amides and esters include, but are not limited to, Examples 6, 7, 11, 12, 40, 41, 42, 43, 51, 55, and 56.

Compositions of the Invention

The invention also provides pharmaceutical compositions comprising of compounds of the invention, or pharmaceutically acceptable salts, amides, esters, prodrugs, or salts of prodrugs thereof, formulated together with one or more pharmaceutically acceptable carriers.

The compounds identified by the methods described hereinabove may be administered as the sole pharmaceutical agent or in combination with one or more other pharmaceutical agents where the combination causes no unacceptable adverse effects. For example, the compounds of this invention can be combined with an atypical antipsychotic. Specific examples of suitable atypical antipsychotics include, but are not limited to, clozapine, risperidone, olanzapine, quietapine, ziprasidone, zotepine, iloperidone, and the like. Thus, the present invention also includes pharmaceutical compositions which are comprised of therapeutically effective amount of compounds identified by the methods described herein, or pharmaceutically acceptable salts, prodrugs or salts of prodrugs thereof, one or more pharmaceutical agents as disclosed hereinabove, and one or more pharmaceutically acceptable carriers.

The pharmaceutical compositions of this invention can be formulated and administered to humans and other mammals orally, rectally, parenterally, intracisternally, intravaginally, intraperitoneally, topically (as by powders, ointments or drops), bucally or as an oral or nasal spray. The pharmaceutical compositions can be formulated for oral administration in solid, semi-solid or liquid form.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that releases the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as benzenesulfonic acid, gluconic acid, oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, and piperazine.

Compounds of the invention may exist as prodrugs. Prodrugs of the invention can be rapidly transformed in vivo to a parent compound of the invention, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof may be converted through in vivo biotransformation into compounds of formula (I).

Methods of the Invention

Compounds and compositions of the invention are useful for modulating the effects of NNRs, and more particularly α7 NNRs, α4β2 NNRs, or both α7 and α4β2 NNRs. In particular, the compounds and compositions of the invention can be used for treating or preventing disorders modulated by α7 NNRs, or α4β2 NNRs, or both α7 and α4β2 NNRs. Typically, such disorders can be ameliorated by selectively modulating the α7 NNRs, α4β2 NNRs, or both α7 and α4β2 NNRs in a mammal, preferably by administering a compound or composition of the invention, either alone or in combination with one or more additional pharmaceutical agents, for example, as part of a therapeutic regimen.

Compounds for the method of the invention, including but not limited to those specified in the examples or otherwise specifically named, can modulate, and often possess an affinity for, NNRs, and more particularly α7 NNRs, α4β2 NNRs, or both α7 and α4β2 NNRs. As α7 NNRs, α4β2 NNRs, or both α7 and α4β2 NNRs ligands, the compounds of the invention can be useful for the treatment or prevention of a number of α7 NNR, α4β2 NNR, or both α7 and α4β2 NNR mediated diseases or conditions.

Specific examples of compounds that can be useful for the treatment or prevention of α7, α4β2 or both α7 and α4β2 NNRs mediated diseases or conditions include, but are not limited to, compounds described in the Compounds of the Invention and also in the Examples.

Methods for preparing compounds useful in the method of the invention also can be found in Iriepa, I, et al. *J. Molec. Struct.* 1999, 509, 105; Flynn, D. L., et al. *Bioorganic & Medicinal Chemistry Letters,* 1992, 2, 1613; U.S. Pat. No. 4,816,453; WO 94/00454; U.S. Pat. Nos. 5,280,028; 5,399, 562; WO 92/15593; U.S. Pat. Nos. 5,260,303; 5,591,749; 5,434,151; and U.S. Pat. No. 5,604,239.

For example, α7 NNRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, ADHD, AD, mild cognitive impairment, senile dementia, AIDS dementia, Pick's disease, dementia associated with Lewy bodies, and dementia associated with Down's syndrome, as well as CDS.

In addition, α7-containing NNRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 NNRs by β-amyloid peptides linked to Alzheimer's disease has been implicated as a key factor in development of the cognitive deficits associated with the disease (Liu, Q.-S., Kawai, H., Berg, D. K., Proc. Natl. Acad. Sci. USA 98: 4734-4739, 2001). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of α7 NNRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

α7 NNRs also have been implicated in aspects of neurodevelopment, for example neurogenesis of the brain (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 NNRs can be useful in preventing or treating conditions or disorders associated with impaired neurodevelopment, for example schizophrenia. (Sawa A., Mol. Med. 9:3-9, 2003).

Several compounds with high affinity for α4β2 NNRs have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at α4β2 NNRs, is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; Biederman, J.; Spencer, T. J.; Bostic, J.; Prince, J.; Monuteaux, M. C.; Soriano, J.; Fince, C.; Abrams, A.; Rater, M.; Polisner, D. The American Journal of Psychiatry (1999)156(12), 1931-1937.). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline have shown efficacy in a pilot clinical trials (Wilens, T. E.; Verlinden, M. H.; Adler, L. A.; Wozniak, P. J.; West, S. A. Biological Psychiatry (2006), 59(11), 1065-1070. Geerts, H. Curr. Opin. Invest. Drugs (2006), 7(1), 60-69.). In addition to cognition, compounds that interact with α4β2 NNRs such as ABT-594 and others are also efficacious in preclinical and clinical models of pain. As such, ligands that modulate both α7 and α4β2 activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of α7 NNRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 NNR (Adler L. E. et al., Schizophrenia Bull. 24: 189-202, 1998; Stevens, K. E. et al., Psychopharmacology 136: 320-327, 1998). More recent studies have shown that α4β2 nicotinic receptor stimulation also contributes to the effects of nicotine in the DBA/2 mouse model of sensory gating (Radek et al., Psychopharmacology (Berl). 2006 187:47-55). Thus, α7 and α7/α4β2 ligands demonstrate potential in the treatment schizophrenia.

A population of α7 or α4β2 NNRs in the spinal cord modulate neurotransmission that has been associated with the pain-relieving effects of nicotinic compounds (Cordero-Erausquin, M. and Changeux, J.-P. Proc. Natl. Acad. Sci. USA 98:2803-2807, 2001). The α7 NNR or and α7/α4β2 ligands demonstrate therapeutic potential for the treatment of pain states, including acute pain, post-surgical pain, as well as chronic pain states including inflammatory pain and neuropathic pain.

Compounds of the invention are particularly useful for treating and preventing a condition or disorder affecting memory, cognition, neurodegeneration, neurodevelopment, and schizophrenia.

Cognitive impairment associated with schizophrenia (CDS) often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol. Psychiatry, 51: 349-357, 2002). Thus, activators of α7 receptors can provide useful treatment for enhancing cognitive function in schizophrenic patients who are being treated with atypical antipsychotics. Accordingly, the combination of an α7 NNR ligand and one or more atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Compounds of the invention may be administered alone or in combination (i.e. co-administered) with one or more additional pharmaceutical agents. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salts, esters, amides, prodrugs, or salts of prodrugs thereof. Compounds of the invention can also be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) is exemplified in Schemes 4-6, wherein the groups $G^1$, $Y^1$ and A are as defined in the Detailed Description of the Invention and Definition of Terms, unless otherwise noted.

As used in the descriptions of the schemes and the examples, certain abbreviations are intended to have the following meanings: BSS for balanced salt solution, dba for dibenzylideneacetone, DMAP for 4-di(methylamino)pyridine, dppf for 1,1'-bis(diphenylphosphino)ferrocene, MeOH for methanol, OAc for acetate, Ph for phenyl, Tris for tris (hydroxymethyl)aminomethane, HPLC for high pressure liquid chromatography and TLC for thin layer chromatography.

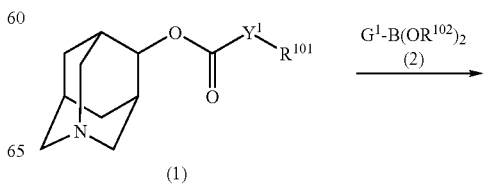

Scheme 4

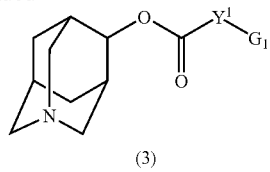

(3)

As shown in Scheme 4, compounds of formula (I) wherein $Y^1$ is A, —N($R^X$)-A or —C($R^Y$)=C($R^Z$)-A, and A is aryl or heteroaryl, and $R^{101}$ is halogen or triflate, can be converted to compounds of formula (3) by reacting with boronic acids or esters of formula (2) wherein $G^1$ is aryl or heteroaryl and $R^{102}$ is hydrogen or alkyl. The reaction typically requires the use of a base and a catalyst. Examples of bases include but are not limited to $K_2CO_3$, potassium tert-butoxide, $Na_2CO_3$, $Cs_2CO_3$, and CsF. Examples of catalysts include but are not limited to $Pd(PPh_3)_4$, $PdCl_2(dppf).CH_2Cl_2$, $Pd_2(dba)_3$, $Pd(OAc)_2$, and $PdCl_2(PPh_3)_2$. Optionally, a ligand, such as but not limited to dicyclohexyl(2'6'-dimethoxybiphenyl-2-yl) phosphine or N,N'-bis(2,6-diisopropylphenyl)imidazol-2-ylidene, may be used. The reaction can be conducted in a solvent such as but not limited to water, dioxane, dimethoxyethane, N,N-dimethylformamide, toluene, ethanol, tetrahydrofuran, or mixtures thereof, and at ambient or elevated temperatures.

Compounds of formula (3) wherein $G^1$ is a heterocycle having the nitrogen atom in the ring attached to $Y^1$, can be prepared by treating compounds of formula (I) wherein $R^{101}$ is halogen or triflate, with heterocyclic amines of formula $G^1$-H wherein the proton is attached to the nitrogen atom in the ring, in the presence of a palladium catalyst, a ligand, and a base. Examples of bases are as listed in the preceding paragraph. An example of the palladium catalyst is tris(dibenzylideneacetone)dipalladium(0). An example of the ligand is 4,5-bis(diphenylphosphino)-9,9-dimethylxanthene. The reaction can be conducted in a solvent as described in the preceding paragraph.

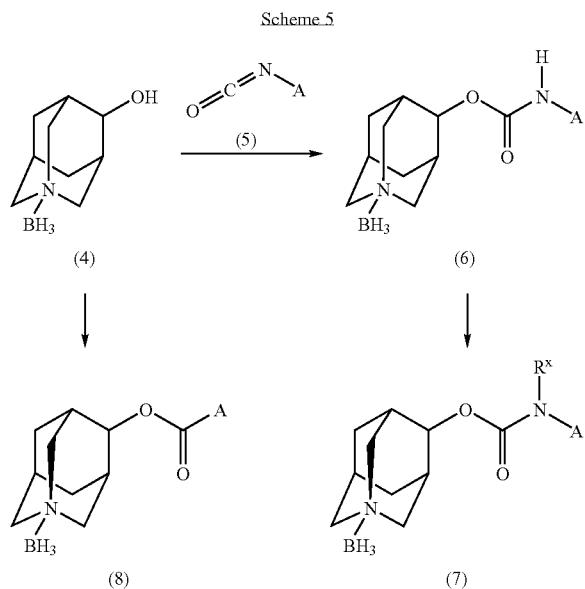

As shown in Scheme 5,1-azaadamantan-4-ol N-borane complex (4) (prepared as in Example 1A), when treated with isocyanates of formula (5) will provide carbamates of formula (6). The reaction is typically conducted in a solvent such as but not limited to toluene, tetrahydrofuran, dichloromethane, N,N-dimethylformamide, and ether. The reaction may be conducted at ambient or elevated temperatures. Compounds of formula (6) can be further alkylated with compounds of formula $R^X$—$R^{103}$ wherein $R^X$ is alkyl or haloalkyl, and $R^{103}$ is a leaving group such as halide, triflate or tosylate, in the presence of a base, to provide compounds of formula (7). Examples of suitable bases include, but are not limited to, sodium hydride or potassium tert-butoxide. The reaction is generally conducted in a solvent such as, but not limited to, tetrahydrofuran, N,N-dimethylformamide, and dimethyl sulfoxide, at ambient or elevated temperatures.

Also shown in Scheme 5,1-azaadamantan-4-ol N-borane complex (4) can be converted to esters of formula (8), by treating with carboxylic acids of formula ACOOH using methodologies analogous to those known to one skilled in the art. For example, the reaction can be performed in the presence of 4-dimethylaminopyridine (DMAP) and a coupling reagent such as but not limited to 1,3-dicyclohexylcarbodiimide (DCC), and N-(3-dimethylaminopropyl)-N'-ethylcarbodiimide hydrochloride (EDAC). The reagents are typically added at 0° C. before warming the mixture to room temperature.

The stereoisomers of the esters or carbamates formed can be separated using conventional techniques such as, but not limited to, silica gel chromatography, at this stage if desired.

Alternatively, individual stereoisomers of compound of formula (4) can be obtained as illustrated in Examples 36A and 37A, and can be used to prepare diastereomerically pure esters and carbamates respectively using general procedures as outlined in Scheme 5.

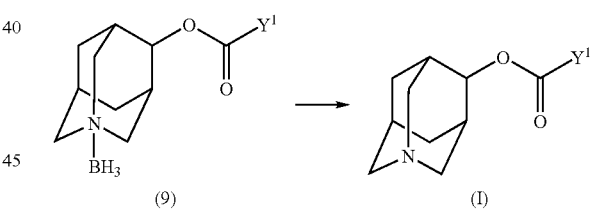

Removal of the borane protecting group of compounds of formula (9) to prepare compounds of formula (I) as shown in Scheme 6 can be accomplished by treatment with an acid such as but not limited to HCl, in a solvent such as, but not limited to, acetone, dioxane or mixtures thereof. The mixture is typically cooled to 0° C. before addition of the acid, and is subsequently warmed to room temperature. The desired compound may be isolated as the HCl salt or the free amine. Alternatively, compounds of formula (9) can be treated with Pd/C in a solvent such as, but not limited to, methanol to provide compounds of formula (I).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Scheme 7

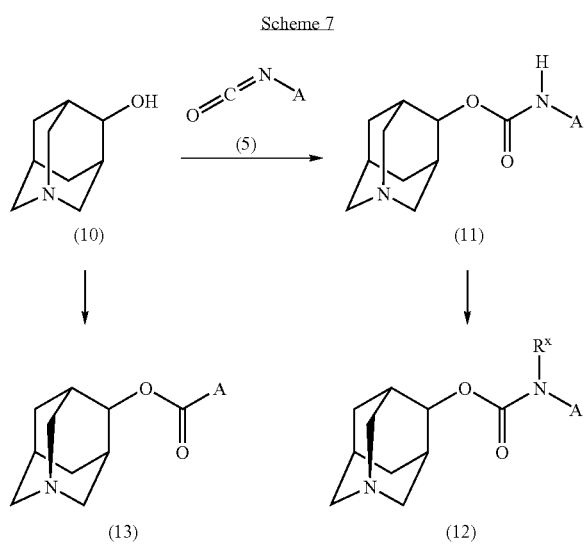

As shown in Scheme 7,1-azaadamantan-4-ol (10) (prepared as in Fernandez, M. J.; Galvez, E.; Lorente, A.; Iriepa, I.; Soler, J. A. Journal of Heterocyclic Chemistry, 1989, 26, 307-312), when treated with isocyanates of formula (5), wherein A is defined for formula (I) will provide carbamates of formula (11). The reaction is typically conducted in a solvent such as but not limited to toluene, tetrahydrofuran, dichloromethane, N,N-dimethylformamide, and ether. The reaction may be conducted at ambient or elevated temperatures. Compounds of formula (11) can be further alkylated with compounds of formula $R^X$—$R^{103}$ wherein $R^X$ is alkyl or haloalkyl, and $R^{103}$ is a leaving group such as halide, triflate or tosylate, in the presence of a base, to provide compounds of formula (12). Examples of suitable bases include, but are not limited to, sodium hydride or potassium tert-butoxide. The reaction is generally conducted in a solvent such as, but not limited to, tetrahydrofuran, N,N-dimethylformamide, and dimethyl sulfoxide, at ambient or elevated temperatures.

Also shown in Scheme 7,1-azaadamantan-4-ol (10) can be converted to esters of formula (13), by treating with carboxylic acids of formula A-COOH using methodologies analogous to those known to one skilled in the art. For example, the reaction can be performed in the presence of 4-dimethylaminopyridine (DMAP) and a coupling reagent such as but not limited to 1,3-dicyclohexylcarbodiimide (DCC), and N-(3-dimethylaminopropyl)-N'-ethylcarbodiimide hydrochloride (EDAC). The reagents are typically added at 0° C. before warming the mixture to room temperature. Alternatively, the carboxylic acid A-COOH can be converted to an acid chloride A-COCl by treatment with a reagent such as, but not limited to, thionyl chloride or oxalyl chloride, either neat or in a solvent such as toluene, and then reacted with 1-azaadamantan-4-ol in the presence of a base such as diisopropylethylamine in a solvent such as dichloromethane.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The compounds of the invention and processes for making compounds for the method of the invention will be better understood by reference to the following examples, which are intended as an illustration of and not a limitation upon the scope of the invention.

EXAMPLES

Method A: Esterification of 1-Azaadamantan-4-ol N-Borane (Mixture of Isomers)

A mixture of (4s)- and (4r)-1-azaadamantan-4-ol N-borane (1.0 equivalent), an appropriate carboxylic acid (1.2 mmol), and 4-dimethylaminopyridine (0.1 equivalent; Aldrich) in dichloromethane (0.2 M in the alcohol) was chilled to 0° C. and treated with N-(3-dimethylaminopropyl)-N'-ethylcarbodiimide hydrochloride (EDAC; 1.3 equivalent; Aldrich). After 1 hour, the reaction mixture was warmed to room temperature and stirred overnight. The solution was washed quickly with 1 M HCl followed by saturated sodium bicarbonate, and dried over magnesium sulfate. The isomeric products were separated by flash chromatography (Analogix silica gel column, ethyl acetate-hexanes). Usually, the higher $R_f$ product is the (4s) stereoisomer and the lower $R_f$ product is the (4r) stereoisomer.

Method B: Esterification of Stereochemically-Pure 1-Azaadamantan-4-ol N-Borane A solution of either (4s)- or (4r)-1-azaadamantan-4-ol N-borane (1.0 equivalent), an appropriate carboxylic acid (1.2 mmol), and 4-dimethylaminopyridine (0.1 equivalent; Aldrich) in dichloromethane (0.2 M in the alcohol) was chilled to 0° C. and treated with N-(3-dimethylaminopropyl)-N'-ethylcarbodiimide hydrochloride (EDAC; 1.3 equivalent; Aldrich). After 1 hour, the reaction mixture was warmed to room temperature and stirred overnight. The solution was washed quickly with 1 M HCl followed by saturated sodium bicarbonate, dried over magnesium sulfate, and purified by flash chromatography (Analogix silica gel column, 5-95% gradient of ethyl acetate-hexanes).

Method C: Anhydrous HCl-Mediated Deboronation to Produce Salt

A solution of a 1-azaadamantane N-borane complex (1 equivalent) in acetone-ethyl acetate (1:1, ~0.5 M) was chilled to 0° C. and treated with HCl-dioxane (4 M; 4 equivalents; Aldrich). After 15 minutes, the ice bath was removed and the mixture was stirred for 2 hours. The resulting solid precipitate was collected by filtration, washed with ethyl acetate and dried under vacuum to provide the hydrochloride salt.

Method D: Aqueous HCl-Mediated Deboronation to Produce Free Base

A suspension of a 1-azaadamantane N-borane complex (1 equivalent) in acetone (~0.5 M) was chilled to 0° C. and treated with 3 N HCl (4 equivalents). After 15 minutes, the ice bath was removed and the mixture was stirred until no more starting material was evident by TLC (the borane complexes can be visualized with basic $KMnO_4$ stain). The solution was then diluted with chloroform, washed with saturated sodium bicarbonate (3×), and dried over anhydrous magnesium sulfate. The resulting material was purified by either flash chromatography [Analogix pre-packed silica gel cartridges, 5-50% gradient of ammonium hydroxide-methanol-chloroform (2:20:78) in chloroform] or by preparative HPLC [Waters XTerra® RP18 column, 5 µm, 30×100 mm, flow rate 40 mL/minutes, 5-95% gradient over 22 minutes of acetonitrile in buffer (0.1 M aqueous ammonium bicarbonate, adjusted to pH 10 with ammonium hydroxide)] to afford the desired product as its free base. (Stotter, P. L.; Friedman, M. D.; Dorsey, G. O.; Shiely, R. W.; Williams, R. F.; Minter, D. E. *Heterocycles* 1987, 25, 251)

Method E: Suzuki Coupling

A flask with a septum cap was charged with a an appropriate halide (1 equivalent), an appropriate boronic acid or boronate ester (2 equivalents), potassium carbonate (4 equivalents), and tetrakis(triphenylphosphine)palladium(0) (0.04 equivalent; Strem Chemical). The flask was sealed, evacuated, flushed with nitrogen, and charged with the solvent mixture 1,4-dioxane-water (3:1; ~0.1 M of the halide), added through the septum. The mixture was then warmed to 90° C. for 3-8 hours. Upon completion of the reaction, the mixture was diluted with ethyl acetate and washed with water, and the extracts were dried over magnesium sulfate and filtered. The resulting material was purified by preparative HPLC [Waters XTerra® RP18 column, 5 µm, 30×100 mm, flow rate 40 mL/minute, 5-95% gradient of acetonitrile in buffer (0.1 M aqueous ammonium bicarbonate, adjusted to pH 10 with ammonium hydroxide), with UV detection at 254 nm]. Fractions containing the desired product were combined, concentrated under vacuum, diluted with methanol or ethyl acetate, and filtered to afford the desired product.

Method F: Salt Formation

A rapidly stirring solution of the free base in ethyl acetate-ethanol or ethanol was treated with either p-toluenesulfonic acid monohydrate (1 equivalent; Aldrich; added as a solution in ethyl acetate) or HCl-dioxane (1-2 equivalent; 4 M; Aldrich) at room temperature. After stirring for 2-16 hours, the precipitate was collected by filtration, rinsed with ethyl acetate, and dried to afford the p-toluenesulfonate salt or the hydrochloride salt.

Method G: Carbamate Formation

A solution of either (4s)- or (4r)-1-azadamantan-4-ol N-borane (1.0 equivalent) and an appropriate isocyanate (1.0 equivalent) in toluene was stirred at 100° C. overnight. The volatiles were removed under reduced pressure and the residue was diluted with dichloromethane, washed with saturated sodium carbonate (3×), and dried over magnesium sulfate. The resulting material was purified by flash chromatography (Analogix silica gel column, 5-60% gradient of ethyl acetate-hexanes).

Example 1

(4s)-(4-Chlorobenzoyloxy)-1-azatricyclo[3.3.1.1$^{3,7}$]decane

Example 1A

1-Azaadamantan-4-ol N-borane Complex

A solution of 1-azaadamantan-4-one (29 g, 190 mmol; prepared as described in Becker, D. P.; Flynn, D. L. *Synthesis* 1992, 1080) in anhydrous tetrahydrofuran (200 mL) was chilled in an ice-water bath, and treated with borane-tetrahydrofuran complex (1.0 M in tetrahydrofuran; 200 mL, 200 mmol; Aldrich) added dropwise. After stirring for 20 minutes, the reaction mixture was diluted with methanol (1000 µL) and carefully treated with sodium borohydride (8.8 g, 230 mmol; Aldrich), keeping the internal temperature of the mixture at about 5-7° C. The reaction was stirred for 2 hours, and then the ice bath was removed and stirring was continued for 4 hours. The volatile components were removed on the rotary evaporator and the residue was dissolved in chloroform (~500 mL) and washed with saturated aqueous sodium carbonate. The aqueous layer was extracted with chloroform and the combined organic phases were dried over magnesium sulfate. The resulting material was purified by flash chromatography (Analogix 400 g 65×220 mm silica gel column, 5-95% gradient of ethyl acetate in hexanes over 50 minutes) to afford an inseparable mixture of isomers.

Example 1B (4s)-(4-Chlorobenzoyloxy)-1-azatricyclo[3.3.1.1$^{3,7}$]decane N-borane Complex and (4r)-(4-Chlorobenzoyloxy)-1-azatricyclo[3.3.1.1$^{3,7}$]decane N-borane Complex Prepared from Example 1A (28 g, 170 mmol), 4-chlorobenzoic acid (28.0 g, 179 mmol; Aldrich), 4-dimethylaminopyridine (4.2 g, 34 mmol; Aldrich), N-(3-dimethylaminopropyl)-N'-ethylcarbodiimide hydrochloride (EDAC; 42.0 g, 219 mmol; Aldrich) in dichloromethane (700 mL) according to Method A. The crude material was purified in ~5 g batches by flash chromatography (Analogix 400 g 65×220 mm silica gel column, 5-55% gradient of ethyl acetate in hexanes over 45 minutes).

(4s) stereoisomer TLC $R_f$=0.49 (silica gel, 3:1 hexanes-ethyl acetate). $^1$H NMR (300 MHz, chloroform-d) δ ppm 1.76 (d, J=12.5 Hz, 2 H), 2.06 (s, 1 H), 2.16-2.33 (m, 4 H), 3.12-3.32 (m, 6 H), 5.26 (t, J=3.2 Hz, 1 H), 7.45 (dt, J=8.7, 2.4, 2.1 Hz, 2 H), 8.00 (dt, J=8.7, 2.4, 2.1 Hz, 2 H). MS (DCI/NH$_3$) m/z=321 (M+16)$^+$, 323 (M+16)$^+$. Anal. Calcd. for C$_{16}$H$_{21}$BClNO$_2$: C, 62.88; H, 6.93; N, 4.58. Found: C, 63.00; H, 6.80; N, 4.50.

(4r) stereoisomer TLC $R_f$=0.34 (silica gel, 3:1 hexanes-ethyl acetate). $^1$H NMR (300 MHz, chloroform-d) δ ppm 1.84-2.11 (m, 5 H), 2.24 (s, 2 H), 3.03 (d, J=12.5 Hz, 2 H), 3.14 (s, 2 H), 3.46 (d, J=13.2 Hz, 2 H), 5.16 (t, J=3.2 Hz, 1 H), 7.39-7.51 (m, 2 H), 7.89-8.05 (m, 2 H). MS (DCI/NH$_3$) m/z=321 (M+16)$^+$, 323 (M+16)$^+$. Anal. Calcd. for C$_{16}$H$_{21}$BClNO$_2$: C, 62.88; H, 6.93; N, 4.58. Found: C, 62.83; H, 6.95; N, 4.53.

Example 1C (4s)-(4-Chlorobenzoyloxy)-1-azatricyclo[3.3.1.1$^{3,7}$]decane

Prepared from the (4s) isomer of Example 1B (210 mg, 0.69 mmol) according to Method D. $^1$H NMR (300 MHz, methanol-d$_4$) δ ppm 1.73 (s, 1 H), 1.93 (d, J=12.2 Hz, 2 H), 2.06 (s, 2 H), 2.33 (d, J=12.9 Hz, 2 H), 3.10-3.22 (m, 4 H), 3.24-3.31 (m, 2 H), 5.32 (t, J=3.2 Hz, 1 H), 7.46-7.59 (m, 2 H), 7.98-8.13 (m, 2 H). MS (DCI/NH$_3$) m/z=292 (M+H)$^+$, 294 (M+H)$^+$.

Example 1D (4s)-(4-Chlorobenzoyloxy)-1-azatricyclo[3.3.1.1$^{3,7}$]decane

Prepared as the hydrochloride salt from the product of Example IC (175 mg, 0.60 mmol) and HCl-dioxane (4.0 M, 0.15 mL, 0.60 mmol) according to Method F. $^1$H NMR (300 MHz, methanol-d$_4$) δ ppm 2.00 (d, J=13.6 Hz, 2 H), 2.23 (s, 2 H), 2.37 (d, J=13.2 Hz, 2 H), 2.49 (s, 2 H), 3.59 (s, 2 H), 3.62-3.76 (m, 4 H), 5.43 (t, J=3.2 Hz, 1 H), 7.51-7.58 (m, 2 H), 8.04-8.11 (m, 2 H). MS (DCI/NH$_3$) m/z=292 (M+H)$^+$, 294 (M+H)$^+$. Anal. Calcd. for C$_{16}$H$_{18}$ClNO$_2$.HCl: C, 58.55; H, 5.83; N, 4.27. Found: C, 58.72; H, 5.80; N, 4.26.

Example 2

(4r)-(4-Chlorobenzoyloxy)-1-azatricyclo[3.3.1.1$^{3,7}$]decane

Example 2A (4r)-(4-Chlorobenzoyloxy)-1-azatricyclo[3.3.1.1$^{3,7}$]decane

Prepared from the (4r) isomer of Example 1B (79 mg, 0.26 mmol) according to Method D. $^1$H NMR (300 MHz, methanol-d$_4$) δ ppm 1.72-1.78 (m, 1 H), 1.94-2.10 (m, 4 H), 2.16-2.26 (m, 2 H), 3.05 (dd, J=12.9, 1.4 Hz, 2 H), 3.17 (s, 2 H), 3.48 (d, J=13.6 Hz, 2 H), 5.31 (t, J=3.4 Hz, 1 H), 7.49-7.55 (m, 2 H), 8.02-8.08 (m, 2 H). MS (DCI/NH$_3$) m/z=292 (M+H)$^+$, 294 (M+H)$^+$.

Example 2B (4r)-(4-Chlorobenzoyloxy)-1-azatricyclo[3.3.1.1$^{3,7}$]decane

Prepared as the hydrochloride salt from the product of Example 2A (50 mg, 0.17 mmol) and HCl-dioxane (4.0 M, 0.043 mL, 0.17 mmol) according to Method F. $^1$H NMR (300 MHz, methanol-d$_4$) δ ppm 2.06-2.17 (m, 2 H), 2.20-2.30 (m, 3 H), 2.47 (s, 2 H), 3.47-3.55 (m, 2 H), 3.57 (s, 2 H), 3.83 (d, J=12.5 Hz, 2 H), 5.32 (t, J=3.4 Hz, 1 H), 7.50-7.57 (m, 2 H), 8.06-8.13 (m, 2 H), MS (DCI/NH$_3$) m/z=292 (M+H)$^+$, 294 (M+H)$^+$. Anal. Calcd. for C$_{16}$H$_{18}$ClNO$_2$.HCl.0.1 H$_2$O: C, 58.23; H, 5.86; N, 4.24. Found: C, 57.99; H, 5.84; N, 4.20.

Example 3

(4s)-(6-Chloronicotinoyloxy)-1-azatricyclo[3.3.1.1$^{3,7}$]decane

Example 3A (4s)-(6-Chloronicotinoyloxy)-1-azatricyclo[3.3.1.1$^{3,7}$]decane N-borane Complex and (4r)-(6-Chloronicotinoyloxy)-1-azatricyclo[3.3.1.1$^{3,7}$]decane N-borane Complex Prepared from the product of Example 1A (668 mg, 4.00 mmol) and 6-chloronicotinic acid (756 mg, 4.80 mmol; Aldrich) according to Method A.

(4s) stereoisomer. $^1$H NMR (300 MHz, chloroform-d) δ ppm 1.53 (s, 3 H), 1.70-1.86 (m, 2 H), 1.98-2.11 (m, 2 H), 2.13-2.41 (m, 4 H), 3.15-3.43 (m, 5 H), 5.30 (t, J=3.6 Hz, 1 H), 7.46 (d, J=8.1 Hz, 1 H), 8.26 (dd, J=8.3, 2.5 Hz, 1 H), 9.03 (d, J=1.7 Hz, 1 H). MS (DCI/NH$_3$) m/z=307 (M+H)$^+$, 309 (M+H)$^+$.

(4r) stereoisomer. $^1$H NMR (300 MHz, chloroform-d) δ ppm 1.83-2.12 (m, 5 H), 2.18-2.39 (m, 2 H), 2.91-3.24 (m, 4 H), 3.33-3.55 (m, 2 H), 5.20 (t, J=3.4 Hz, 1 H), 7.46 (d, J=8.1 Hz, 1 H), 8.23 (dd, J=8.3, 2.5 Hz, 1 H), 9.02 (d, J=2.4 Hz, 1 H). MS (DCI/NH$_3$) m/z=307 (M+H)$^+$, 309 (M+H)$^+$.

Example 3B (4s)-(6-Chloronicotinoyloxy)-1-azatricyclo[3.3.1.1$^{3,7}$]decane

Prepared as the hydrochloride salt from the (4s) isomer of Example 3A (730 mg, 2.38 mmol) according to Method C. $^1$H NMR (300 MHz, methanol-d$_4$) δ ppm 1.90-2.11 (m, 2 H), 2.17-2.29 (m, 1 H), 2.32-2.47 (m, 2 H), 2.47-2.58 (m, 2 H), 3.53-3.82 (m, 6 H), 5.44-5.51 (m, 1 H), 7.63 (d, J=8.4 Hz, 1 H), 8.41 (dd, J=8.4, 2.37 Hz, 1 H), 9.02 (d, J=2.4 Hz, 1 H). MS (DCI/NH$_3$) m/z=293 (M+H)$^+$, 295 (M+H)$^+$. Anal. Calcd. for C$_{15}$H$_{17}$ClN$_2$O$_2$.HCl.0.5 H$_2$O: C, 53.27; H, 5.66; N, 8.28. Found: C, 53.04; H, 5.36; N, 8.02.

Example 4

(4r)-(6-Chloronicotinoyloxy)-1-azatricyclo[3.3.1.1$^{3,7}$]decane

Prepared as the hydrochloride salt from the (4r) isomer of Example 3A (320 mg, 1.04 mmol) according to Method C. $^1$H NMR (300 MHz, methanol-d$_4$) δ ppm 2.10-2.16 (m, 2 H), 2.18-2.33 (m, 3 H), 2.43-2.57 (m, 2 H), 3.45-3.63 (m, 4 H), 3.77-3.92 (m, 2 H), 5.36 (t, J=3.4 Hz, 1 H), 7.62 (d, J=8.5 Hz, 1 H), 8.44 (dd, J=8.5, 2.4 Hz, 1 H), 9.04 (d, J=1.7 Hz, 1 H). MS (DCI/NH$_3$) m/z=293 (M+H)$^+$, 295 (M+H)$^+$. Anal. Calcd. for C$_{15}$H$_{17}$ClN$_2$O$_2$.2.2HCl.1.3 H$_2$O: C, 45.45; H, 5.54; N, 7.07. Found: C, 45.06; H, 5.20; N, 6.87.

Example 5

(4r)-(6-Phenylnicotinoyloxy)-1-azatricyclo[3.3.1.1$^{3,7}$]decane

Example 5A (4r)-(6-Phenylnicotinoyloxy)-1-azatricyclo[3.3.1.1$^{3,7}$]decane Prepared from the product of Example 4 (150 mg, 0.456 mmol) and phenylboronic acid (83 mg, 0.68 mmol; Aldrich) according to Method E. $^1$H NMR (300 MHz, methanol-d$_4$) δ ppm 1.71-1.86 (m, 1 H), 1.95-2.14 (m, 4 H), 2.17-2.31 (m, 2 H), 2.99-3.14 (m, 2 H), 3.16-3.27 (m, 2 H), 3.44-3.63 (m, 2 H), 5.23-5.47 (m, 1 H), 7.42-7.59 (m, 3 H), 8.02 (d, J=7.5 Hz, 1 H), 8.05-8.14 (m, 2 H), 8.47 (dd, J=8.3, 2.2 Hz, 1 H), 9.24 (d, J=2.4 Hz, 1 H). MS (DCI/NH$_3$) m/z=335 (M+H)$^+$.

Example 5B (4r)-(6-Phenylnicotinoyloxy)-1-azatricyclo[3.3.1.1$^{3,7}$]decane Prepared as the hydrochloride salt from the product of Example 5A (80 mg, 0.24 mmol) and HCl-dioxane (4 M; 0.2 mL, 0.80 mmol) according to Method F. $^1$H NMR (300 MHz, methanol-d$_4$) δ ppm 2.05-2.19 (m, 2 H), 2.22-2.41 (m, 3 H), 2.46-2.65 (m, 2 H), 3.46-3.77 (m, 4 H), 3.84-4.21 (m, 2 H), 5.44 (t, J=3.2 Hz, 1 H), 7.54-7.82 (m, 3 H), 7.96-8.19 (m, 2 H), 8.35 (d, J=8.5 Hz, 1 H), 8.96 (dd, J=8.5, 2.37 Hz, 1 H), 9.38 (d, J=2.4 Hz, 1 H). MS (DCI/NH$_3$) m/z=335 (M+H)$^+$. Anal. Calcd. for C$_{21}$H$_{22}$N$_2$O$_2$.2HCl 0.5 H$_2$O: C, 60.58; H, 6.05; N, 6.73. Found: C, 60.79; H, 5.91; N, 6.69.

Example 6

(4s)-[6-(Indol-5-yl)nicotinoyloxy]-1-azatricyclo[3.3.1.1$^{3,7}$]decane

Example 6A (4s)-[6-(Indol-5-yl)nicotinoyloxy]-1-azatricyclo[3.3.1.1$^{3,7}$]decane Prepared from the product of Example 3B (150 mg, 0.456 mmol) and indol-5-ylboronic acid (110 mg, 0.683 mmol) according to Method E. $^1$H NMR (300 MHz, DMSO-d$_6$) δ ppm 1.52-1.66 (m, 1 H), 1.79-1.90 (m, 2 H), 1.91-1.98 (m, 2 H), 2.20-2.36 (m, 2 H), 2.96-3.09 (m, 4 H), 3.11-3.22 (m, 2 H), 5.28 (t, J=3.2 Hz, 1 H), 6.56 (d, J=2.0 Hz, 1 H), 7.38-7.46 (m, 1 H), 7.51 (d, J=8.8 Hz, 1 H), 7.97 (dd, J=8.5, 1.7 Hz, 1 H), 8.12 (d, J=7.8 Hz, 1 H), 8.34 (dd, J=8.3, 2.2 Hz, 1 H), 8.42 (d, J=1.7 Hz, 1 H), 9.18 (d, J=2.4 Hz, 1 H), 11.30 (s, 1 H). MS (DCI/NH$_3$) m/z=374 (M+H)$^+$.

Example 6B (4s)-[6-(Indol-5-yl)nicotinoyloxy]-1-azatricyclo[3.3.1.1$^{3,7}$]decane Prepared as the hydrochloride salt from the product of Example 6A (90 mg, 0.24 mmol) and HCl-dioxane (4 M; 0.2 mL, 0.8 mmol) according to Method F. $^1$H NMR (300 MHz, methanol-d$_4$) δ ppm 1.95-2.16 (m, 2 H), 2.21-2.33 (m, 1 H), 2.39-2.52 (m, 2 H), 2.52-2.67 (m, 2 H), 3.56-3.86 (m, 6 H), 5.57 (t, J=3.1 Hz, 1 H), 6.72 (dd, J=3.4, 0.7 Hz, 1 H), 7.45 (t, J=1.5 Hz, 1 H), 7.68 (d, J=8.4 Hz, 1 H), 7.82 (dd, J=6.4, 2.1 Hz, 1 H), 8.38 (d, J=2.0 Hz, 1 H), 8.49 (d, J=8.5 Hz, 1 H), 8.96 (dd, J=8.8, 2.0 Hz, 1 H), 9.19 (d, J=2.0 Hz, 1 H); MS (DCI/NH$_3$) m/z=374 (M+H)$^+$. Anal. Calcd. for C$_{23}$H$_{23}$N$_3$O$_2$.2HCl 0.8 H$_2$O: C, 59.95; H, 0.82; N, 9.12. Found: C, 59.93; H, 5.68; N, 9.05.

Example 7

(4r)-[6-(Indol-5-yl)nicotinoyloxy]-1-azatricyclo[3.3.1.1$^{3,7}$]decane

Example 7A (4r)-[6-(Indol-5-yl)nicotinoyloxy]-1-azatricyclo[3.3.1.1$^{3,7}$]decane Prepared from the product of Example 4 (150 mg, 0.456 mmol) and indol-5-ylboronic acid (110 mg, 0.683 mmol) according to Method E. $^1$H NMR (300 MHz, DMSO-d$_6$) δ ppm 1.52-1.66 (m, 1 H), 1.80-1.90 (m, 2 H), 1.90-2.03 (m, 2 H), 2.04-2.16 (m, 2 H), 2.85-2.99 (m, 2H), 2.99-3.09 (m, 2 H), 3.35-3.48 (m, 2 H), 5.16-5.48 (m, 1 H), 6.56 (d, J=2.4 Hz, 1 H), 7.37-7.46 (m, 1 H), 7.51 (d, J=8.5 Hz, 1 H), 7.97 (dd, J=8.7, 1.9 Hz, 1 H), 8.11 (d, J=8.5 Hz, 1 H), 8.36 (dd, J=8.3, 2.2 Hz, 1 H), 8.42 (d, J=1.4 Hz, 1 H), 9.19 (d, J=2.0 Hz, 1 H), 11.30 (s, 1 H). MS (DCI/NH$_3$) m/z=374 (M+H)$^+$.

Example 7B (4r)-[6-(Indol-5-yl)nicotinoyloxy]-1-azatricyclo[3.3.1.1$^{3,7}$]decane The product of Example 7A (80 mg, 0.21 mmol) was treated with HCl-dioxane (4 M; 0.2 mL, 0.8 mmol) according to Method F to afford the title compound as a hydrochloride salt. $^1$H NMR (300 MHz, methanol-d$_4$) δ ppm 2.05-2.39 (m, 5 H), 2.45-2.72 (m, 2 H), 3.46-3.71 (m, 4 H), 3.83-4.02 (m, 2 H), 5.44 (t, J=3.4 Hz, 1 H), 6.69 (d, J=3.4 Hz, 1 H), 7.44 (d, J=3.4 Hz, 1 H), 7.66 (d, J=8.5 Hz, 1 H), 7.82 (dd, J=8.7, 1.9 Hz, 1 H), 8.36 (d, J=2.0 Hz, 1 H), 8.41 (d, J=8.8 Hz, 1 H), 8.91 (dd, J=8.5, 2.0 Hz, 1 H), 9.26 (d, J=1.4 Hz, 1 H). MS (DCI/NH$_3$) m/z=374 (M+H)$^+$. Anal. Calcd. for C$_{23}$H$_{23}$N$_3$O$_2$.2HCl.1.1H$_2$O: C, 59.26; H, 5.88; N, 9.01. Found: C, 59.09; H, 5.87; N, 8.74.

Example 8

(4s)-(5-Bromonicotinoyloxy)-1-azatricyclo[3.3.1.1$^{3,7}$]decane

Example 8A (4s)-(5-Bromonicotinoyloxy)-1-azatricyclo[3.3.1.1$^{3,7}$]decane N-borane complex
and (4r)-(5-Bromonicotinoyloxy)-1-azatricyclo[3.3.1.1$^{3,7}$]decane N-borane complex Prepared from the product of Example 1A (668 mg, 4.00 mmol) and 5-bromonicotinic acid (969 mg, 4.80 mmol; Aldrich) according to Method A.

(4s) stereoisomer. $^1$H NMR (300 MHz, chloroform-d) δ ppm 1.57 (s, 3 H), 1.68-1.88 (m, 2 H), 2.01-2.17 (m, 1 H), 2.16-2.39 (m, 4 H), 3.11-3.42 (m, 6 H), 5.21-5.38 (m, 1 H), 8.37-8.53 (m, 1 H), 8.88 (d, J=2.4 Hz, 1 H), 9.16 (d, J=1.7 Hz, 1 H). MS (DCI/NH$_3$) m/z=351 (M+H)$^+$, 353 (M+H)$^+$.

(4r) stereoisomer. $^1$H NMR (300 MHz, chloroform-d) δ ppm 1.54 (s, 3 H), 1.82-2.15 (m, 5 H), 2.23-2.34 (m, 2 H), 2.97-3.11 (m, 2 H), 3.10-3.18 (m, 2 H), 3.33-3.61 (m, 2 H), 5.20 (t, J=3.2 Hz, 1 H), 8.40 (t, J=2.0 Hz, 1 H), 8.89 (s, 1 H), 9.14 (s, 1 H). MS (DCI/NH$_3$) m/z=351 (M+H)$^+$, 353 (M+H)$^+$.

Example 8B (4s)-(5-Bromonicotinoyloxy)-1-azatricyclo[3.3.1.1$^{3,7}$]decane

Prepared as the hydrochloride salt from the (4s) isomer of Example 8A (920 mg, 2.62 mmol) according to Method C. $^1$H NMR (300 MHz, methanol-d$_4$) δ ppm 1.90-2.12 (m, 2 H), 2.19-2.31 (m, 1 H), 2.33-2.47 (m, 2 H), 2.45-2.68 (m, 2 H), 3.50-3.82 (m, 6 H), 5.49 (t, J=3.2 Hz, 1 H), 8.67 (t, J=1.9 Hz, 1 H), 8.99 (d, J=2.4 Hz, 1 H), 9.20 (d, J=1.70 Hz, 1 H). MS (DCI/NH$_3$) m/z=337 (M+H)$^+$, 339 (M+H)$^+$. Anal. Calcd. for C$_{15}$H$_{17}$BrN$_2$O$_2$.2HCl.2.1H$_2$O: C, 40.22; H, 5.22; N, 6.25. Found: C, 39.92; H, 4.87; N, 6.06.

Example 9

(4r)-(5-Bromonicotinoyloxy)-1-azatricyclo[3.3.1.1$^{3,7}$]decane

Prepared as the hydrochloride salt from the (4r) isomer of Example 8A (300 mg, 0.855 mmol) according to Method C. $^1$H NMR (300 MHz, DMSO-d$_6$) δ ppm 1.84-2.04 (m, 2 H), 2.04-2.17 (m, 3 H), 2.29-2.39 (m, 2 H), 3.30-3.49 (m, 4 H), 3.68-3.89 (m, J=12.2 Hz, 2 H), 5.22 (t, J=3.2 Hz, 1 H), 8.61-8.73 (m, 1 H), 9.00 (d, J=2.4 Hz, 1 H), 9.21 (d, J=1.7 Hz, 1 H), 10.43 (s, 1 H). MS (DCI/NH$_3$) m/z=337 (M+H)$^+$, 339 (M+H)$^+$. Anal. Calcd. for C$_{15}$H$_{17}$BrN$_2$O$_2$.2HCl.1.4H$_2$O: C, 41.38; H, 5.05; N, 6.43. Found: C, 41.24; H, 4.66; N, 6.17.

Example 10

(4r)-(5-Phenylnicotinoyloxy)-1-azatricyclo[3.3.1.1$^{3,7}$]decane

Example 10A (4r)-(5-Phenylnicotinoyloxy)-1-azatricyclo[3.3.1.1$^{3,7}$]decane Prepared from the product of Example 9 (150 mg, 0.401 mmol) and phenylboronic acid (73 mg, 0.60 mmol; Aldrich) according to Method E. $^1$H NMR (300 MHz, methanol-d$_4$) δ ppm 2.07-2.20 (m, 2 H), 2.20-2.36 (m, 3 H), 2.44-2.67 (m, 2 H), 3.46-3.72 (m, 4 H), 3.79-4.03 (m, 2 H), 5.40 (t, J=3.4 Hz, 1 H), 7.36-7.62 (m, 3 H), 7.66-7.82 (m, 2 H), 8.65 (t, J=2.0 Hz, 1 H), 9.05 (d, J=2.4 Hz, 1 H), 9.20 (d, J=2.0 Hz, 1 H). MS (DCI/NH$_3$) m/z=335 (M+H)$^+$.

Example 10B (4r)-(5-Phenylnicotinoyloxy)-1-azatricyclo[3.3.1.1$^{3,7}$]decane Prepared as the hydrochloride salt from the product of Example 10A (130 mg, 0.389 mmol) and HCl-dioxane (4 M; 0.5 mL, 2.0 mmol) according to Method F. $^1$H NMR (300 MHz, methanol-d$_4$) δ ppm 2.04-2.41 (m, 5 H), 2.47-2.65 (m, 2 H), 3.46-3.73 (m, 4 H), 3.84-4.18 (m, 2 H), 5.46 (t, J=3.2 Hz, 1 H), 7.50-7.75 (m, 3 H), 7.80-7.98 (m, 2 H), 9.30 (t, J=1.9 Hz, 1H), 9.37 (d, J=2.0 Hz, 1 H), 9.50 (d, J=1.7 Hz, 1 H). MS (DCI/NH$_3$) m/z=335 (M+H)$^+$.

Example 11

(4s)-[5-(Indol-5-yl)nicotinoyloxy]-1-azatricyclo[3.3.1.1$^{3,7}$]decane

Example 11A (4s)-[5-(Indol-5-yl)nicotinoyloxy]-1-azatricyclo[3.3.1.1$^{3,7}$]decane Prepared from the product of Example 8B (150 mg, 0.401 mmol) and indol-5-ylboronic acid (97 mg, 0.60 mmol) according to Method E. $^1$H NMR (300 MHz, methanol-d$_4$) δ ppm 1.95-2.19 (m, 3 H), 2.32-2.53 (m, 4 H), 3.40-3.69 (m, 6 H), 5.29-5.75 (m, 1 H), 6.57 (d, J=3.0 Hz, 1 H), 7.32 (d, J=3.0 Hz, 1 H), 7.45 (dd, J=6.1, 2.0 Hz, 1 H), 7.55 (d, J=8.5 Hz, 1 H), 7.91 (s, 1 H), 8.63 (t, J=2.2 Hz, 1 H), 9.08 (dd, J=6.1, 2.0 Hz, 2 H). MS (DCI/NH$_3$) m/z=374 (M+H)$^+$.

Example 11B (4s)-[5-(Indol-5-yl)nicotinoyloxy]-1-azatricyclo[3.3.1.1$^{3,7}$]decane Prepared as the hydrochloride salt from the product Example 11A (30 mg, 0.08 mmol) and HCl-dioxane (4 M; 0.1 mL, 0.4 mmol) according to Method F. $^1$H NMR (300 MHz, methanol-d$_4$) δ ppm 1.96-2.12 (m, 2 H), 2.20-2.33 (m, 1 H), 2.39-2.52 (m, 2 H), 2.53-2.67 (m, 2 H), 3.55-3.86 (m, 6 H), 5.46-5.75 (m, 1 H), 6.62 (d, J=3.0 Hz, 1 H), 7.37 (d, J=3.4 Hz, 1H,) 7.51-7.74 (m, 2 H), 8.08 (s, 1 H), 9.12-9.18 (m, 1 H), 9.25 (d, J=1.7 Hz, 1 H), 9.31 (d, J=1.7 Hz, 1 H). MS (DCI/NH$_3$) m/z=374 (M+H)$^+$. Anal. Calcd. for C$_{23}$H$_{23}$N$_3$O$_2$.2HCl.2.5H$_2$O: C, 56.22; H, 6.15; N, 8.55. Found: C, 55.82; H, 5.85; N, 8.15.

Example 12

(4r)-[5-(Indol-5-yl)nicotinoyloxy]-1-azatricyclo[3.3.1.1$^{3,7}$]decane

Example 12A (4r)-[5-(Indol-5-yl)nicotinoyloxy]-1-azatricyclo[3.3.1.1$^{3,7}$]decane Prepared from the product of Example 9 (150 mg, 0.401 mmol) and indol-5-ylboronic acid (97 mg, 0.60 mmol) according to Method E. $^1$H NMR (300 MHz, methanol-d$_4$) δ ppm 1.85-1.97 (m, 1 H), 2.05-2.18 (m, 2 H), 2.25-2.38 (m, 4 H), 3.18-3.28 (m, 4 H), 3.55-3.73 (m, 2H), 5.31-5.51 (m, 1 H), 6.56 (d, J=3.4 Hz, 1 H), 7.32 (d, J=3.4 Hz, 1 H), 7.41-7.48 (m, 1 H), 7.51-7.59 (m, 1 H), 7.84-7.98 (m, 1 H), 8.63 (t, J=2.0 Hz, 1 H), 9.07 (m, 2 H). MS (DCI/NH$_3$) m/z=374 (M+H)$^+$.

Example 12B (4r)-[5-(Indol-5-yl)nicotinoyloxy]-1-azatricyclo[3.3.1.1$^{3,7}$]decane Prepared as the hydrochloride salt from the product of Example 12A (140 mg, 0.375 mmol) and HCl-dioxane (4 M; 0.5 mL, 2.0 mmol) according to Method F. $^1$H NMR (300 MHz, methanol-d$_4$) δ ppm 2.10-2.18 (m, 2 H), 2.22-2.38 (m, 3 H), 2.52-2.58 (m, 2 H), 3.93-4.04 (m, 2 H), 5.47 (t, J=3.4 Hz, 1 H), 6.62 (d, J=3.4 Hz, 1 H), 7.33-7.42 (m, 1 H), 7.61 (s, 2 H), 8.12 (s, 1 H), 9.28 (d, J=1.7 Hz, 1 H), 9.35 (d, J=6.4 Hz, 2 H). MS (DCI/NH$_3$) m/z=374 (M+H)$^+$. Anal. Calcd. for C$_{23}$H$_{23}$N$_3$O$_2$.2.9HCl: C, 57.65; H, 5.45; N, 8.77. Found: C, 57.68; H, 5.34; N, 8.57.

Example 13

(4s)-(Furan-2-oyloxy)-1-azatricyclo[3.3.1.1$^{3,7}$]decane

Prepared as the hydrochloride salt from the product of Example 1A and 2-furoic acid (Aldrich) according to Methods A and C. $^1$H NMR (300 MHz, methanol-d$_4$) δ 2.05-2.15 (m, 2H), 2.19-2.29 (m, 3 H), 2.44 (s, 2 H), 3.46-3.58 (m, 4 H), 3.78 (d, J=12.5 Hz, 2 H), 5.29 (t, J=3.6 Hz, 1 H), 6.64 (dd, J=3.4, 1.7 Hz, 1 H), 7.40 (dd, J=3.4, 0.7 Hz, 1 H), 7.79 (dd, J=1.7, 1.0 Hz, 1 H). MS (DCI/NH$_3$) m/z 248 (M+H)$^+$. Anal. Calcd. for C$_{14}$H$_{17}$NO$_3$.HCl1.25H$_2$O: C, 54.90; H, 6.75; N, 4.57. Found: C, 54.77; H, 6.35; N, 4.56.

Example 14

(4r)-(Furan-2-oyloxy)-1-azatricyclo[3.3.1.1$^{3,7}$]decane

Prepared as the hydrochloride salt from the product of Example 1A and 2-furoic acid (Aldrich) according to Methods A and C. $^1$H NMR (300 MHz, methanol-d$_4$) δ 1.95 (s, 1 H), 1.99 (s, 1H), 2.21 (s, 1 H), 2.33 (s, 1 H), 2.37 (s, 1 H), 2.46 (s, 2 H), 3.58 (s, 2 H), 3.60-3.75 (m, 4H), 5.39 (t, J=3.4 Hz, 1 H), 6.65 (dd, J=3.7, 1.7 Hz, 1 H), 7.36 (dd, J=3.6, 0.8 Hz, 1 H), 7.79 (d, J=1.7 Hz, 1 H). MS (DCI/NH$_3$) m/z 248 (M+H)$^+$. Anal. Calcd. for C$_{14}$H$_{17}$NO$_3$.HCl.0.3H$_2$O: C, 58.15; H, 6.48; N, 4.84. Found: C, 58.18; H, 6.28; N, 4.80.

Example 15

(4s)-(5-Bromofuran-2-oyloxy)-1-azatricyclo[3.3.1.1$^{3,7}$]decane

Prepared as the hydrochloride salt from the product of Example 1A and 5-bromo-2-furoic acid (Aldrich) according to Methods A and C. $^1$H NMR (300 MHz, methanol-d$_4$) δ 2.04-2.14 (m, 2 H), 2.18-2.29 (m, 3 H), 2.44 (s, 2 H), 3.45-3.58 (m, 4H), 3.77 (d, J=12.9 Hz, 2 H), 5.28 (t, J=3.4 Hz, 1 H), 6.67 (d, J=3.7 Hz, 1 H), 7.38 (d, J=3.7 Hz, 1 H). MS (DCI/NH$_3$) m/z 325 (M+H)$^+$, 327 (M+H)$^+$. Anal. Calcd. for C$_{14}$H$_{16}$BrNO$_3$.HCl: C, 46.37; H, 4.72; N, 3.86. Found: C, 46.41; H, 4.47; N, 3.84.

Example 16

(4r)-(5-Bromofuran-2-oyloxy)-1-azatricyclo[3.3.1.1$^{3,7}$]decane

Prepared as the hydrochloride salt from the product of Example 1A and 5-bromo-2-furoic acid (Aldrich) according to Methods A and C. $^1$H NMR (300 MHz, methanol-d$_4$) δ 1.97 (d, J=12.5 Hz, 2 H), 2.21 (s, 1 H), 2.34 (d, J=13.6 Hz, 2 H), 2.46 (s, 2 H), 3.58 (s, 2 H), 3.60-3.75 (m, 4 H), 5.39 (t, J=3.4 Hz, 1 H), 6.67 (d, J=3.7 Hz, 1 H), 7.35 (d, J=3.7 Hz, 1 H). MS (DCI/NH$_3$) m/z 325 (M+H)$^+$, 327 (M+H)$^+$. Anal. Calcd. for C$_{14}$H$_{16}$BrNO$_3$.HCl.0.33 H$_2$O: C, 45.62; H, 4.83; N, 3.80. Found: C, 45.54 H, 5.08; N, 3.54.

Example 17

(4s)-(4,5-Dimethylfuran-2-oyloxy)-1-azatricyclo[3.3.1.1$^{3,7}$]decane

Prepared as the hydrochloride salt from the product of Example 1A and 4,5-dimethyl-2-furoic acid (Maybridge) according to Methods A and C. $^1$H NMR (300 MHz, methanol-d$_4$) δ 2.00 (s, 3 H), 2.03-2.15 (m, 2 H), 2.18-2.26 (m, 3 H), 2.29 (s, 3 H), 2.41 (s, 2 H), 3.44-3.59 (m, 4 H), 3.76 (d, J=12.5 Hz, 2 H), 5.23 (t, J=3.4 Hz, 1 H), 7.19 (s, 1H). MS (DCI/NH$_3$) m/z 276 (M+H)$^+$. Anal. Calcd. for C$_{16}$H$_{21}$NO$_3$.HCl.0.3H$_2$O: C, 60.58; H, 7.18; N, 4.42. Found: C, 60.59; H, 7.05; N, 4.34.

Example 18

(4r)-(4,5-Dimethylfuran-2-oyloxy)-1-azatricyclo[3.3.1.1$^{3,7}$]decane

Prepared as the hydrochloride salt from the product of Example 1A and 4,5-dimethyl-2-furoic acid (Maybridge) according to Methods A and C. $^1$H NMR (300 MHz, methanol-d$_4$) δ 1.89-2.09 (m, 5 H), 2.20 (s, 1 H), 2.26-2.37 (m, 5 H), 2.43 (s, 2 H), 3.57 (s, 2 H), 3.60-3.74 (m, 4 H), 5.33 (t, J=3.4 Hz, 1 H), 7.15 (s, 1 H). MS (DCI/NH$_3$) m/z 276 (M+H)$^+$. Anal. Calcd. for C$_{16}$H$_{21}$NO$_3$.HCl: C, 61.63; H, 7.11; N, 4.49. Found: C, 61.30; H, 7.04; N, 4.48.

Example 19

(4s)-(Thiophen-2-oyloxy)-1-azatricyclo[3.3.1.1$^{3,7}$]decane

Prepared as the hydrochloride salt from the product of Example 1A and 2-thiophenecarboxylic acid (Aldrich) according to Methods A and C. $^1$H NMR (300 MHz, methanol-d$_4$) δ 2.07-2.17 (m, 2 H), 2.18-2.31 (m, 3 H), 2.46 (s, 2 H), 3.47-3.62 (m, 4 H), 3.77 (d, J=12.9 Hz, 2 H), 5.28 (t, J=3.6 Hz, 1 H), 7.20 (dd, J=5.1, 3.7 Hz, 1 H), 7.81 (dd, J=5.1, 1.4 Hz, 1 H), 7.93 (dd, J=3.9, 1.2 Hz, 1 H). MS (DCI/NH$_3$) m/z 264 (M+H)$^+$. Anal. Calcd. for C$_{14}$H$_{17}$NO$_2$S.HCl.0.6 H$_2$O: C, 54.13; H, 6.23; N, 4.51. Found: C, 54.11; H, 6.35; N, 4.39.

Example 20

(4r)-(Thiophen-2-oyloxy)-1-azatricyclo[3.3.1.1$^{3,7}$]decane

Prepared as the hydrochloride salt from the product of Example 1A and 2-thiophenecarboxylic acid (Aldrich) according to Methods A and C. $^1$H NMR (300 MHz, methanol-d$_4$) δ 1.99 (d, J=12.5 Hz, 2 H), 2.23 (s, 1 H), 2.35 (d, J=12.9 Hz, 2 H), 2.48 (s, 2 H), 3.58 (s, 2 H), 3.63-3.80 (m, 4 H), 5.39 (t, J=3.4 Hz, 1 H), 7.20 (dd, J=5.1, 3.7 Hz, 1 H), 7.82 (dd, J=5.1, 1.4 Hz, 1 H), 7.91 (dd, J=3.9, 1.2 Hz, 1 H). MS (DCI/NH$_3$) m/z 264 (M+H)$^+$. Anal. Calcd. for C$_{14}$H$_{17}$NO$_2$S.HCl.0.15 H$_2$O: C, 55.58; H, 6.10; N, 4.63. Found: C, 55.58; H, 6.10; N, 4.59.

Example 21

(4s)-(Thiophen-3-oyloxy)-1-azatricyclo[3.3.1.1$^{3,7}$]decane

Prepared as the hydrochloride salt from the product of Example 1A and thiophene-3-carboxylic acid (Alfa Aesar) according to Methods A and C. $^1$H NMR (300 MHz, methanol-d$_4$) δ 2.04-2.15 (m, 2 H), 2.18-2.30 (m, 3 H), 2.44 (s, 2 H), 3.44-3.61 (m, 4 H), 3.82 (d, J=12.9 Hz, 2 H), 5.27 (t, J=3.4 Hz, 1 H), 7.52 (s, 1 H), 7.58 (s, 1 H), 8.39 (s, 1 H). MS (DCI/NH$_3$) m/z 264 (M+H)$^+$. Anal. Calcd. for C$_{14}$H$_{17}$NO$_2$S.HCl: C, 56.08; H, 6.05; N, 4.67. Found: C, 56.10; H, 6.14; N, 4.56.

Example 22

(4r)-(Thiophen-3-oyloxy)-1-azatricyclo[3.3.1.1$^{3,7}$]decane

Prepared as the hydrochloride salt from the product of Example 1A and thiophene-3-carboxylic acid (Alfa Aesar) according to Methods A and C. $^1$H NMR (300 MHz, methanol-d$_4$) δ 1.99 (d, J=13.6 Hz, 2 H), 2.23 (s, 1 H), 2.38 (d, J=13.2 Hz, 2 H), 2.47 (s, 2 H), 3.59 (s, 2 H), 3.68 (s, 4 H), 5.37 (t, J=3.4 Hz, 1 H), 7.49-7.55 (m, 1 H), 7.55-7.61 (m, 1 H), 8.35 (d, J=3.1 Hz, 1 H). MS (DCI/NH$_3$) m/z 264 (M+H)$^+$. Anal. Calcd. for C$_{14}$H$_{17}$NO$_2$S.HCl: C, 56.08; H, 6.05; N, 4.67. Found: C, 55.89; H, 6.04; N, 4.61.

Example 23

(4s)-(5-Chlorothiophen-2-oyloxy)-1-azatricyclo[3.3.1.1$^{3,7}$]decane

Prepared as the hydrochloride salt from the product of Example 1A and 5-chlorothiophene-2-carboxylic acid (Aldrich) according to Methods A and C. $^1$H NMR (300 MHz, methanol-d$_4$) δ 2.04-2.15 (m, 2 H), 2.17-2.29 (m, 3 H), 2.44 (s, 2 H), 3.45-3.59 (m, 4H), 3.75 (d, J=12.5 Hz, 2 H), 5.27 (t, J=3.6 Hz, 1 H), 7.12 (d, J=4.1 Hz, 1 H), 7.77 (d, J=4.1 Hz, 1 H). MS (DCI/NH$_3$) m/z 298 (M+H)$^+$. Anal. Calcd. for C$_{14}$H$_{16}$ClNO$_2$S.HCl: C, 50.31; H, 5.13; N, 4.19. Found: C, 50.15; H, 4.98; N, 4.15.

Example 24

(4r)-(5-Chlorothiophen-2-oyloxy)-1-azatricyclo[3.3.1.1$^{3,7}$]decane

Prepared as the hydrochloride salt from the product of Example 1A and 5-chlorothiophene-2-carboxylic acid (Aldrich) according to Methods A and C. $^1$H NMR (300 MHz, methanol-d$_4$) δ 1.97 (s, 1 H), 2.01 (s, 1 H), 2.22 (s, 1 H), 2.30 (s, 1 H), 2.34 (s, 1 H), 2.46 (s, 2 H), 3.58 (s, 2 H), 3.61-3.74 (m, 4 H), 5.38 (t, J=3.4 Hz, 1 H), 7.13 (d, J=4.1 Hz, 1 H), 7.74 (d, J=4.1 Hz, 1 H). MS (DCI/NH$_3$) m/z 298 (M+H)$^+$. Anal. Calcd. for C$_{14}$H$_{16}$ClNO$_2$S.HCl: C, 50.31; H, 5.13; N, 4.19. Found: C, 50.24; H, 4.98; N, 4.11.

Example 25

(4s)-(5-Methylthiophen-2-oyloxy)-1-azatricyclo[3.3.1.1$^{3,7}$]decane

Prepared as the hydrochloride salt from the product of Example 1A and 5-methylthiophene-2-carboxylic acid (Aldrich) according to Methods A and C. $^1$H NMR (300 MHz, methanol-d$_4$) δ 1.99-2.15 (m, 2 H), 2.17-2.29 (m, 3 H), 2.44 (s, 2 H), 2.54 (s, 3 H), 3.41-3.66 (m, 4 H), 3.75 (d, J=12.5 Hz, 2 H), 5.24 (t, J=3.6 Hz, 1 H), 6.89 (d, J=3.7 Hz, 1 H), 7.73 (d, J=3.7 Hz, 1 H). MS (DCI/NH$_3$) m/z 278 (M+H)$^+$. Anal. Calcd. for C$_{15}$H$_{19}$NO$_2$S.HCl.0.25 H$_2$O: C, 56.59; H, 6.49; N, 4.40. Found: C, 56.88; H, 6.67; N, 4.12.

Example 26

(4r)-(5-Methylthiophen-2-oyloxy)-1-azatricyclo[3.3.1.1$^{3,7}$]decane

Prepared as the hydrochloride salt from the product of Example 1A and 5-methylthiophene-2-carboxylic acid (Aldrich) according to Methods A and C. $^1$H NMR (300 MHz, methanol-d$_4$) δ 1.96 (s, 3 H), 2.00 (s, 1 H), 2.22 (s, 1 H), 2.31 (s, 1 H), 2.36 (s, 1 H), 2.45 (s, 2 H), 2.55 (s, 3 H), 3.57 (s, 2 H), 3.60-3.74 (m, 4 H), 5.35 (t, J=3.4 Hz, 1 H), 6.90 (dd, J=3.7, 1.0 Hz, 1 H), 7.71 (d, J=3.7 Hz, 1 H). MS (DCI/NH$_3$) m/z 278 (M+H)$^+$. Anal. Calcd. for C$_{15}$H$_{19}$NO$_2$S.HCl: C, 57.41; H, 6.42; N, 4.46. Found: C, 57.56; H, 6.68; N, 4.38.

Example 27

(4s)-(5-Bromothiophen-2-oyloxy)-1-azatricyclo[3.3.1.1$^{3,7}$]decane

Prepared as the hydrochloride salt from the product of Example 1A and 5-bromothiophene-2-carboxylic acid (Lancaster) according to Methods A and C. $^1$H NMR (300 MHz, methanol-d$_4$) δ 1.98-2.16 (m, 2 H), 2.17-2.30 (m, 3 H), 2.44 (s, 2 H), 3.43-3.61 (m, 4H), 3.75 (d, J=12.5 Hz, 2 H), 5.27 (t, J=3.6 Hz, 1 H), 7.25 (d, J=4.1 Hz, 1 H), 7.72 (d, J=4.1 Hz, 1 H). MS (DCI/NH$_3$) m/z 341 (M+H)$^+$, 343 (M+H)$^+$. Anal. Calcd. for C$_{14}$H$_{16}$BrNO$_2$S.HCl: C, 44.40; H, 4.52; N, 3.70. Found: C, 44.47; H, 4.26; N, 3.49.

Example 28

(4r)-(5-Bromothiophen-2-oyloxy)-1-azatricyclo[3.3.1.1$^{3,7}$]decane

Prepared as the hydrochloride salt from the product of Example 1A and 5-bromothiophene-2-carboxylic acid (Lancaster) according to Methods A and C. $^1$H NMR (300 MHz, methanol-d$_4$) δ 1.97 (s, 1 H), 2.01 (s, 1 H), 2.22 (s, 1 H), 2.30 (s, 1 H), 2.34 (s, 1 H), 2.46 (s, 2 H), 3.58 (s, 2 H), 3.60-3.75 (m, 4 H), 5.37 (t, J=3.4 Hz, 1 H), 7.25 (d, J=4.1 Hz, 1 H), 7.69 (d, J=4.1 Hz, 1 H). MS (DCI/NH$_3$) m/z 341 (M+H)$^+$, 343 (M+H)$^+$. Anal. Calcd. for C$_{14}$H$_{16}$BrNO$_2$S.HCl: C, 44.40; H, 4.52; N, 3.70. Found: C, 44.47; H, 4.45; N, 3.58.

Example 29

(4s)-(3-Bromothiophen-2-oyloxy)-1-azatricyclo[3.3.1.1$^{3,7}$]decane

Prepared as the hydrochloride salt from the product of Example 1A and 3-bromothiophene-2-carboxylic acid (Aldrich) according to Methods A and C. $^1$H NMR (300 MHz, methanol-d$_4$) δ 2.05-2.16 (m, 2 H), 2.19-2.32 (m, 3 H), 2.47 (s, 2 H), 3.48-3.62 (m, 4H), 3.83 (d, J=12.5 Hz, 2 H), 5.35 (t, J=3.4 Hz, 1 H), 7.21 (d, J=5.4 Hz, 1 H), 7.82 (d, J=5.4 Hz, 1 H). MS (DCI/NH$_3$) m/z 341 (M+H)$^+$, 343 (M+H)$^+$. Anal. Calcd. for C$_{14}$H$_{16}$BrNO$_2$S.HCl.0.4H$_2$O: C, 43.57; H, 4.65; N, 3.63. Found: C, 43.52; H, 4.38; N, 3.59.

Example 30

(4r)-(3-Bromothiophen-2-oyloxy)-1-azatricyclo[3.3.1.1$^{3,7}$]decane

Prepared as the hydrochloride salt from the product of Example 1A and 3-bromothiophene-2-carboxylic acid (Aldrich) according to Methods A and C. $^1$H NMR (300 MHz, methanol-d$_4$) δ 2.00 (d, J=13.6 Hz, 2 H), 2.23 (s, 1 H), 2.44 (d, J=21.7 Hz, 4 H), 3.58 (s, 2 H), 3.63-3.75 (m, 4 H), 5.44 (t, J=3.2 Hz, 1 H), 7.21 (d, J=5.1 Hz, 1 H), 7.81 (d, J=5.1 Hz, 1 H). MS (DCI/NH$_3$) m/z 341 (M+H)$^+$, 343 (M+H)$^+$. Anal. Calcd. for C$_{14}$H$_{16}$BrNO$_2$S.HCl: C, 44.40; H, 4.52; N, 3.70. Found: C, 44.60; H, 4.33; N, 3.47.

Example 31

(4s)-(5-(2-Thienyl)thiophen-2-oyloxy)-1-azatricyclo[3.3.1.1$^{3,7}$]decane

Prepared as the hydrochloride salt from the product of Example 1A and 2,2'-bithiophen-5-carboxylic acid (Maybridge) according to Methods A and C. $^1$H NMR (300 MHz, methanol-d$_4$) δ 2.04-2.17 (m, 2 H), 2.18-2.32 (m, 3 H), 2.47 (s, 2 H), 3.47-3.62 (m, 4 H), 3.79 (d, J=12.5 Hz, 2 H), 5.29 (t, J=3.4 Hz, 1 H), 7.11 (dd, J=5.1, 3.7 Hz, 1 H), 7.30 (d, J=3.7 Hz, 1H), 7.41 (d, J=3.4 Hz, 1 H), 7.48 (d, J=5.4 Hz, 1 H), 7.85 (d, J=4.1 Hz, 1 H). MS (DCI/NH$_3$) m/z 346 (M+H)$^+$. Anal. Calcd. for C$_{18}$H$_{19}$NO$_2$S$_2$.HCl.0.1H$_2$O: C, 56.34; H, 5.31; N, 3.65. Found: C, 56.26; H, 5.44; N, 3.37.

Example 32

(4r)-(5-(2-Thienyl)thiophen-2-oyloxy)-1-azatricyclo[3.3.1.1$^{3,7}$]decane

Prepared as the hydrochloride salt from the product of Example 1A and 2,2'-bithiophen-5-carboxylic acid (Maybridge) according to Methods A and C. $^1$H NMR (300 MHz, methanol-d$_4$) δ 1.98 (s, 1 H), 2.02 (s, 1 H), 2.23 (s, 1 H), 2.34 (s, 1 H), 2.39 (s, 1 H), 2.48 (s, 2H), 3.58 (s, 2 H), 3.60-3.76 (m, 4 H), 5.39 (t, J=3.6 Hz, 1 H), 7.11 (dd, J=5.1, 3.7 Hz, 1 H), 7.31 (d, J=4.1 Hz, 1 H), 7.42 (dd, J=3.7, 1.0 Hz, 1 H), 7.48 (dd, J=5.1, 1.0 Hz, 1 H), 7.82 (d, J=3.7 Hz, 1 H). MS (DCI/NH$_3$) m/z 346 (M+H)$^+$. Anal. Calcd. for C$_{18}$H$_{19}$NO$_2$S$_2$.HCl: C, 56.60; H, 5.28; N, 3.67. Found: C, 56.63; H, 5.33; N, 3.58.

Example 33

(4s)-1-Azatricyclo[3.3.1.1³,⁷]decan-4-yl 2-(thiophen-2-yl)thiazole-4-carboxylate Prepared as the hydrochloride salt from the product of Example 1A and 2-(2-thienyl)-1,3-thiazole-4-carboxylic acid (Maybridge) according to Methods A and C. $^1$H NMR (300 MHz, methanol-$d_4$) δ 2.00 (d, J=12.2 Hz, 1 H), 2.24 (s, 1 H), 2.43 (d, J=14.2 Hz, 2 H), 2.52 (s, 2 H), 3.59 (s, 2 H), 3.64-3.77 (m, 4 H), 5.45 (t, J=3.4 Hz, 1 H), 7.17 (dd, J=5.1, 3.7 Hz, 1 H), 7.64 (dd, J=5.1, 1.0 Hz, 1 H), 7.72 (dd, J=3.7, 1.4 Hz, 1 H), 8.47 (s, 1 H). MS (DCI/NH$_3$) m/z 347 (M+H)$^+$. Anal. Calcd. for $C_{17}H_{18}N_2O_2S_2 \cdot HCl \cdot 0.5H_2O$: C, 52.10; H, 5.14; N, 7.15. Found: C, 51.98; H, 4.80; N, 6.93.

Example 34

(4r)-1-Azatricyclo[3.3.1.1³,⁷]decan-4-yl 2-(thiophen-2-yl)thiazole-4-carboxylate Prepared as the hydrochloride salt from the product of Example 1A and 2-(2-thienyl)-1,3-thiazole-4-carboxylic acid (Maybridge) according to Methods A and C. $^1$H NMR (300 MHz, methanol-$d_4$) δ 1.98 (s, 1 H), 2.02 (s, 1 H), 2.24 (s, 1 H), 2.41 (s, 1 H), 2.46 (s, 1 H), 2.52 (s, 2H), 3.60 (s, 2 H), 3.70 (s, 4 H), 5.45 (t, J=3.2 Hz, 1 H), 7.17 (dd, J=5.1, 3.7 Hz, 1 H), 7.64 (dd, J=5.1, 1.0 Hz, 1 H), 7.72 (dd, J=3.7, 1.0 Hz, 1 H), 8.48 (s, 1 H). MS (DCI/NH$_3$) m/z 347 (M+H)$^+$. Anal. Calcd. for $C_{17}H_{18}N_2O_2S_2 \cdot HCl \cdot 0.5H_2O$: C, 52.10; H, 5.14; N, 7.15. Found: C, 52.08; H, 4.98; N, 7.04.

Example 35

(4s)-(2-Naphthoyloxy)-1-azatricyclo[3.3.1.1³,⁷]decane

Example 35A (4s)-(2-Naphthoyloxy)-1-azatricyclo[3.3.1.1³,⁷]decane N-borane Complex and (4r)-(2-Naphthoyloxy)-1-azatricyclo[3.3.1.1³,⁷]decane N-borane Complex Prepared from the product of Example 1A (200 mg, 1.20 mmol) and 2-naphthoic acid (220 mg, 1.28 mmol; Aldrich) according to Method A.

(4s) stereoisomer. TLC R$^f$=0.44 (silica gel, 3:1 hexanes-ethyl acetate). $^1$H NMR (300 MHz, methanol-$d_4$) δ ppm 1.83 (d, J=12.9 Hz, 2 H), 2.05 (s, 1 H), 2.26-2.39 (m, 4 H), 3.16-3.27 (m, J=14.9 Hz, 6 H), 5.34 (t, J=3.4 Hz, 1 H), 7.54-7.68 (m, Hz, 2 H), 7.92-8.11 (m, 4 H), 8.66 (s, 1 H). MS (DCI/NH$_3$) m/z 337 (M+16)$^+$.

(4r) stereoisomer. TLC R$_f$=0.31 (silica gel, 3:1 hexanes-ethyl acetate). $^1$H NMR (300 MHz, methanol-$d_4$) δ ppm 1.92-2.12 (m, 5 H), 2.28 (s, 2 H), 3.06 (d, J=12.9 Hz, 2 H), 3.13 (s, 2H), 3.48 (d, J=13.2 Hz, 2 H), 5.23 (t, J=3.4 Hz, 1 H), 7.55-7.68 (m, 2 H), 7.93-8.08 (m, 4 H), 8.64 (s, 1 H). MS (DCI/NH$_3$) m/z 337 (M+16)$^+$.

Example 35B (4s)-(2-Naphthoyloxy)-1-azatricyclo[3.3.1.1³,⁷]decane

Prepared from the (4s) isomer of Example 35A (210 mg, 0.65 mmol) according to Method D. $^1$H NMR (300 MHz, methanol-$d_4$) δ ppm 1.76 (s, 1 H), 1.97 (d, J=12.2 Hz, 2 H), 2.11 (s, 2 H), 2.42 (d, J=12.5 Hz, 2 H), 3.13-3.25 (m, 4 H), 3.27-3.37 (m, 2 H), 5.38 (t, J=3.4 Hz, 1 H), 7.54-7.67 (m, 2 H), 7.91-8.11 (m, 4 H), 8.65 (s, 1 H). MS (DCI/NH$_3$) m/z 308 (M+H)$^+$.

Example 35C (4s)-(2-Naphthoyloxy)-1-azatricyclo[3.3.1.1³,⁷]decane

Prepared as the hydrochloride salt from the product of Example 35B (175 mg, 0.569 mmol) and HCl-dioxane (4 M; 0.14 mL, 0.57 mmol) according to Method F. $^1$H NMR (300 MHz, methanol-$d_4$) δ ppm 2.04 (d, J=12.2 Hz, 2 H), 2.28 (s, 1 H), 2.41-2.60 (m, 4 H), 3.62 (s, 2H), 3.66-3.79 (m, 4 H), 5.49 (t, J=3.2 Hz, 1 H), 7.56-7.69 (m, J=16.2, 8.1, 7.0, 1.7 Hz, 2 H), 7.93-8.12 (m, 4 H), 8.69 (s, 1 H). MS (DCI/NH$_3$) m/z 308 (M+H)$^+$. Anal. Calcd. for $C_{20}H_{21}NO_2 \cdot HCl$: C, 69.86; H, 6.45; N, 4.07. Found: C, 69.90; H, 6.47; N, 4.02.

Example 36

(4s)-(Benzothiophen-5-oyloxy)-1-azatricyclo[3.3.1.1³,⁷]decane

Example 36A (4s)-1-Azatricyclo[3.3.1.1³,⁷]decane N-borane Complex

A suspension of the (4s) isomer of Example 1B (25.0 g, 81.8 mmol) in tetrahydrofuran (50 mL) was treated with 5 M sodium hydroxide (50 mL). After 1 hour, the reaction mixture was warmed to 50° C. for 3 hours. Most of the solvent was removed on the rotary evaporator, and the residue was purified by flash chromatography (Analogix 220 g 65×120 mm silica gel column, 5-95% gradient of ethyl acetate in hexanes) to afford the product. $^1$H NMR (300 MHz, methanol-$d_4$) δ ppm 0.87-2.09 (br m, 3 H; BH$_3$), 1.59 (d, J=12.5 Hz, 2 H), 1.78-1.98 (m, 2 H), 2.22 (d, J=12.5 Hz, 2 H), 2.97-3.18 (m, 6 H), 3.96 (t, J=3.4 Hz, 1 H). MS (DCI/NH$_3$) m/e 183 (M+H)$^+$.

Example 36B (4s)-(Benzothiophen-5-oyloxy)-1-azatricyclo[3.3.1.1³,⁷]decane N-borane Complex Prepared from the product of Example 36A (100 mg, 0.599 mmol) and benzothiophene-5-carboxylic acid (107 mg, 0.599 mmol; Maybridge) according to Method B. $^1$H NMR (300 MHz, chloroform-d) δ ppm 1.77 (d, J=13.6 Hz, 2 H), 2.08 (s, 1 H), 2.26-2.36 (m, 4 H), 3.18-3.34 (m, 6 H), 5.29-5.34 (m, 1 H), 7.45 (d, J=5.1 Hz, 1 H), 7.55 (d, J=5.4 Hz, 1 H), 7.93-8.05 (m, 2 H), 8.55 (d, J=1.0 Hz, 1 H). MS (DCI/NH$_3$) m/e 343 (M+16)$^+$.

Example 36C (4s)-(Benzothiophen-5-oyloxy)-1-azatricyclo[3.3.1.1³,⁷]decane

Prepared as the hydrochloride salt from the product of Example 36B (160 mg, 0.49 mmol) according to Methods D and F. $^1$H NMR (300 MHz, methanol-$d_4$) δ ppm 2.03 (d, J=11.5 Hz, 2 H), 2.26 (s, 1 H), 2.45 (d, J=13.2 Hz, 2 H), 2.53 (s, 2 H), 3.61 (s, 2 H), 3.65-3.78 (m, 4H), 5.47 (t, J=3.2 Hz, 1 H), 7.54 (d, J=5.4 Hz, 1 H), 7.72 (d, J=5.8 Hz, 1 H), 8.00-8.09 (m, 2H), 8.61 (t, J=1.0 Hz, 1 H). MS (DCI/NH$_3$) m/e 314 (M+H)$^+$. Anal. Calcd. for $C_{18}H_{19}NO_2 \cdot HCl$: C, 61.79; H, 5.76; N, 4.00. Found: C, 61.55; H, 5.58; N, 3.91.

Example 37

(4r)-(Benzothiophen-5-oyloxy)-1-azatricyclo[3.3.1.1³,⁷]decane

Example 37A (4r)-1-Azatricyclo[3.3.1.1³,⁷]decane N-borane Complex

A suspension of the (4r) isomer of Example 1B (10.0 g, 32.7 mmol) in tetrahydrofuran (20 mL) was treated with 5 M sodium hydroxide (20 mL) and the reaction mixture was warmed to 50° C. for 4 hours. The reaction was diluted with chloroform and washed with water, and the aqueous phase was extracted with additional chloroform. The product was purified by flash chromatography (Analogix 80 g 40×170 mm silica gel column, 10-95% gradient of ethyl acetate in hexanes) to afford the titled product $^1$H NMR (300 MHz, methanol-$d_4$) δ ppm 0.82-2.02 (br m, 3 H), 1.76 (d, J=11.9 Hz, 2 H), 1.83-1.99 (m, 6 H), 2.81 (d, J=12.2 Hz, 2 H), 3.00 (s, 2 H), 3.37 (d, J=12.9 Hz, 2 H), 3.82 (s, 1 H). MS (DCI/NH$_3$) m/z=183 (M+H)$^+$.

Example 37B (4r)-(Benzothiophen-5-oyloxy)-1-azatricyclo[3.3.1.1$^{3,7}$]decane N-borane Complex Prepared from the product of Example 37A (100 mg, 0.599 mmol) and benzothiophene-5-carboxylic acid (117 mg, 0.656 mmol; Maybridge) according to Method B. $^1$H NMR (300 MHz, chloroform-d) δ ppm 1.89-2.10 (m, 5 H), 2.28 (s, 2 H), 3.05 (dd, J=13.4, 0.8 Hz, 2 H), 3.15 (s, 2 H), 3.55 (d, J=12.9 Hz, 2 H), 5.22 (t, J=3.2 Hz, 1 H), 7.44-7.48 (m, 1H), 7.53-7.58 (m, 1 H), 7.92-8.03 (m, 2 H), 8.52 (d, J=1.0 Hz, 1 H). MS (DCI/NH$_3$) m/z=343 (M+16)$^+$.

Example 37C (4r)-(Benzothiophen-5-oyloxy)-1-azatricyclo[3.3.1.1$^{3,7}$]decane

Prepared as the hydrochloride salt from the product of Example 37B (160 mg, 0.49 mmol) according to Methods D and F. $^1$H NMR (300 MHz, methanol-$d_4$) δ ppm 2.08-2.20 (m, 2 H), 2.21-2.32 (m, 3 H), 2.51 (s, 2 H), 3.49-3.62 (m, 4 H), 3.90 (d, J=12.5 Hz, 2 H), 5.36 (t, J=3.4 Hz, 1 H), 7.53 (d, J=5.4 Hz, 1 H), 7.72 (d, J=5.4 Hz, 1 H), 8.05 (d, J=1.0 Hz, 2 H), 8.65 (s, 1 H). MS (DCI/NH$_3$) m/e 314 (M+H)$^+$. Anal. Calcd. for C$_{18}$H$_{19}$NO$_2$.HCl: C, 61.79; H, 5.76; N, 4.00. Found: C, 61.70; H, 5.83; N, 3.94.

Example 38

(4s)-(Thieno[2,3-c]pyridine-5-oyloxy)-1-azatricyclo[3.3.1.1$^{3,7}$]decane

Example 38A (4s)-(Thieno[2,3-c]pyridine-5-oyloxy)-1-azatricyclo[3.3.1.1$^{3,7}$]decane Prepared from the product of Example 36A (100 mg, 0.599 mmol) and thieno[2,3-c]pyridine-5-carboxylic acid (118 mg, 0.658 mmol; Tetrahedron Lett. 1999, 40, 7935) according to Methods B and D. $^1$H NMR (300 MHz, chloroform-d) δ ppm 1.70 (s, 1 H), 1.90 (d, J=12.2 Hz, 2 H), 2.13 (s, 2 H), 2.40 (d, J=12.9 Hz, 2 H), 3.14-3.25 (m, 4 H), 3.27-3.37 (m, 2 H), 5.44 (t, J=3.4 Hz, 1 H), 7.53 (d, J=5.4 Hz, 1 H), 7.84 (d, J=5.4 Hz, 1 H), 8.58 (d, J=0.7 Hz, 1 H), 9.29 (s, 1 H). MS (DCI/NH$_3$) m/e 315 (M+H)$^+$.

Example 38B (4s)-(Thieno[2,3-c]pyridine-5-oyloxy)-1-azatricyclo[3.3.1.1$^{3,7}$]decane Prepared as the hydrochloride salt from the product of Example 38A (61 mg, 0.19 mmol) and HCl-dioxane (4M; 0.05 mL, 0.0002 mmol) according to Method F. $^1$H NMR (300 MHz, methanol-$d_4$) δ ppm 2.05 (d, J=13.2 Hz, 2 H), 2.28 (s, 1 H), 2.47-2.65 (m, 4 H), 3.63 (s, 2H), 3.68-3.81 (m, 4 H), 5.61 (t, J=3.2 Hz, 1 H), 7.97 (d, J=5.4 Hz, 1 H), 8.65 (d, J=5.4 Hz, 1H), 9.04 (s, 1 H), 9.64 (s, 1 H). Anal. Calcd. for C$_{17}$H$_{18}$N$_2$O$_2$.2 HCl.0.7H$_2$O: C, 51.05; H, 5.39; N, 7.00. Found: C, 50.96; H, 5.35; N, 6.90.

Example 39

(4r)-(Thieno[2,3-c]pyridine-5-oyloxy)-1-azatricyclo[3.3.1.1$^{3,7}$]decane

The hydrochloride salt of the title compound was prepared from the product of Example 37A (100 mg, 0.599 mmol) and thieno[2,3-c]pyridine-5-carboxylic acid (118 mg, 0.658 mmol; Tetrahedron Lett. 1999, 40, 7935) according to Methods B, D, and F. The product was recrystallized from hot acetonitrile. $^1$H NMR (300 MHz, methanol-$d_4$) δ ppm 2.08-2.39 (m, 5H), 2.58 (s, 2 H), 3.51-3.65 (m, 4 H), 4.07 (d, J=12.5 Hz, 2 H), 5.52 (t, J=3.4 Hz, 1 H), 8.04 (d, J=5.4 Hz, 1 H), 8.78 (d, J=5.4 Hz, 1 H), 9.22 (s, 1 H), 9.73 (s, 1 H). MS (DCI/NH$_3$) m/e 315 (M+H)$^+$. Anal. Calcd. for C$_{17}$H$_{18}$N$_2$O$_2$.2HCl.H$_2$O: C, 50.37; H, 5.47; N, 6.91. Found: C, 49.97; H, 5.34; N, 6.85.

Example 40

(4s)-(5-Bromoindol-3-oyloxy)-1-azatricyclo[3.3.1.1$^{3,7}$]decane

Prepared from the product of Example 36A (167 mg, 1.00 mmol) and 5-bromo-1-(tert-butoxycarbonyl)-1 H-indole-3-carboxylic acid (340 mg, 1.00 mmol; Maybridge) according to Methods B and D; then purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-$d_4$) δ ppm 2.01 (s, 1 H), 2.05 (s, 1 H), 2.26 (s, 1 H), 2.38-2.56 (m, 4 H), 3.57-3.77 (m, 6 H), 5.42 (t, J=3.2 Hz, 1 H), 7.32-7.37 (m, 1 H), 7.39-7.44 (m, 1 H), 8.10 (s, 1 H), 8.22 (d, J=2.0 Hz, 1 H). MS (DCI/NH$_3$) m/z 375 (M+H)$^+$, 377 (M+H)$^+$. Anal. Calcd. for C$_{18}$H$_{19}$BrN$_2$O$_2$.C$_2$HF$_3$O$_2$: C, 49.10; H, 4.12; N, 5.73. Found: C, 48.87; H, 4.13; N, 5.68.

Example 41

(4s)-(4-Bromoindol-3-oyloxy)-1-azatricyclo[3.3.1.1$^{3,7}$]decane

Prepared as the trifluoroacetate salt from the product of Example 36A (167 mg, 1.00 mmol) and 4-bromo-1-(tert-butoxycarbonyl)-1 H-indole-3-carboxylic acid (340 mg, 1.00 mmol; Maybridge) according to Methods B and D; then purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-$d_4$) δ ppm 1.96 (s, 1H), 2.00 (s, 1 H), 2.21 (s, 1 H), 2.39 (s, 1 H), 2.44 (s, 1 H), 2.53 (s, 2 H), 3.58 (s, 2 H), 3.69 (s, 4H), 5.35 (t, J=3.1 Hz, 1 H), 7.11 (t, J=8.0 Hz, 1 H), 7.41 (d, J=7.1 Hz, 1 H), 7.48 (d, J=8.1 Hz, 1H), 8.12 (s, 1 H). MS (DCI/NH$_3$) m/z 375 (M+H)$^+$, 377 (M+H)$^+$. Anal. Calcd. for C$_{18}$H$_{19}$BrN$_2$O$_2$.1.1C$_2$HF$_3$O$_2$: C, 48.46; H, 4.05; N, 5.59. Found: C, 48.52; H, 4.10; N, 5.43.

Example 42

(4s)-(Indol-3-oyloxy)-1-azatricyclo[3.3.1.1$^{3,7}$]decane

A solution of the product of Example 40 (62 mg, 0.127 mmol) in methanol (2 mL) was treated with palladium on carbon (10% Pd/C; 15 mg; Aldrich) under a hydrogen balloon atmosphere for 48 hours. After the filtering to remove the catalyst, the residue was purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-d$_4$) δ ppm 2.00 (s, 1 H), 2.04 (s, 1 H), 2.25 (s, 1 H), 2.41-2.57 (m, 4 H), 3.60 (s, 2 H), 3.70 (s, 4 H), 5.42 (t, J=3.2 Hz, 1 H), 7.17-7.27 (m, 2 H), 7.44-7.50 (m, 1 H), 8.05-8.11 (m, 2 H). MS (DCI/NH$_3$) m/z 297 (M+H)$^+$. Anal. Calcd. for C$_{18}$H$_{20}$N$_2$O$_2$.1.1C$_2$F$_3$O$_2$H: C, 57.52; H, 5.04; N, 6.64. Found: C, 57.31; H, 4.77; N, 6.59.

Example 43

(4s)-(Indol-6-oyloxy)-1-azatricyclo[3.3.1.1$^{3,7}$]decane

A solution of 1 H-indole-6-carboxylic acid (161 mg, 1.0 mmol; Aldrich) in anhydrous tetrahydrofuran (5 mL) was treated with di-tert-butyl dicarbonate (437 mg, 2.0 mmol; Aldrich) and 4-dimethylaminopyridine (DMAP; 20 mg, 0.16 mmol; Aldrich) with stirring under nitrogen for 16 hours. After removing the volatiles and drying the solid under vacuum for 1 hour, the residue was dissolved in anhydrous tetrahydrofuran (5 mL) and was treated with Example 36A (334 mg, 2.0 mmol) and N,N'-dicyclohexylcarbodiimide (412 mg, 2.0 mmol; Aldrich). This mixture was stirred at room temperature for 60 hours and then purified by flash chromatography (80 g silica gel column, 3:1 hexanes-ethyl acetate). The resulting N-borane complex was deprotected according to Method D, followed by brief treatment with trifluoroacetic acid (2 mL, Aldrich) to complete removal of the N-tert-butoxycarbonyl group. The product was purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-d$_4$) δ ppm 2.00 (s, 1 H), 2.05 (s, 1 H), 2.26 (s, 1 H), 2.40-2.56 (m, 4 H), 3.56-3.77 (m, 6 H), 5.43 (t, J=3.2 Hz, 1 H), 6.55 (dd, J=3.2, 0.8 Hz, 1 H), 7.47 (d, J=3.1 Hz, 1 H), 7.64 (d, J=8.5 Hz, 1 H), 7.76 (dd, J=8.1, 1.4 Hz, 1 H), 8.20 (d, J=0.7 Hz, 1 H). MS (DCI/NH$_3$) m/z 297 (M+H)$^+$. Anal. Calcd. for C$_{18}$H$_{20}$N$_2$O$_2$.1.05C$_2$F$_3$O$_2$: C, 58.02; H, 5.10; N, 6.73. Found: C, 57.93; H, 5.17; N, 6.65.

Example 44

(4s)-(Benzofuran-5-oyloxy)-1-azatricyclo[3.3.1.1$^{3,7}$]decane

Prepared from the product of Example 1A (0.167 g, 1.00 mmol) and benzofuran-5-carboxylic acid (162 mg, 1.0 mmol; Apollo) according to Method A. The resulting N-borane complex was deprotected according to Method D, and the product was purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-d$_4$) δ ppm 2.00 (s, 1 H), 2.04 (s, 1 H), 2.26 (s, 1 H), 2.39-2.56 (m, 4 H), 3.57-3.78 (m, 6 H), 5.45 (t, J=3.2 Hz, 1 H), 6.99 (dd, J=2.4, 1.0 Hz, 1 H), 7.63 (d, J=8.5 Hz, 1 H), 7.89 (d, J=2.4 Hz, 1H), 8.08 (dd, J=8.5, 1.7 Hz, 1 H), 8.43 (d, J=1.7 Hz, 1 H). MS (DCI/NH$_3$) m/z 298 (M+H)$^+$. Anal. Calcd. for C$_{18}$H$_{19}$NO$_3$.1.2C$_2$HF$_3$O$_2$: C, 56.43; H, 4.69; N, 3.23. Found: C, 56.49; H, 4.59; N, 3.30.

Example 45

(4r)-(Benzothiophen-3-oyloxy)-1-azatricyclo[3.3.1.1$^{3,7}$]decane

Prepared from the product of Example 1A (0.167 g, 1.00 mmol) and benzo[b]thiophene-3-carboxylic acid (178 mg, 1.0 mmol; Maybridge) according to Method A. The resulting N-borane complex was deprotected according to Method D, and the product was purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-d$_4$) δ ppm 2.10-2.33 (m, 5 H), 2.52 (s, 2 H), 3.50-3.61 (m, 4 H), 3.87 (s, 1 H), 3.91 (s, 1 H), 5.37 (t, J=3.6 Hz, 1 H), 7.41-7.55 (m, 2 H), 7.95-7.99 (m, 1 H), 8.54-8.59 (m, 1 H), 8.76 (s, 1 H). MS (DCI/NH$_3$) m/z 314 (M+H)$^+$. Anal. Calcd. for C$_{18}$H$_{19}$NO$_2$S.1.15C$_2$HF$_3$O$_2$: C, 54.85; H, 4.57; N, 3.15. Found: C, 54.84; H, 4.38; N, 3.13.

Example 46

(4s)-(5-Methoxy-2-methylbenzofuran-3-oyloxy)-1-azatricyclo[3.3.1.1$^{3,7}$]decane Prepared from the product of Example 1A (0.167 g, 1.00 mmol) and 5-methoxy-2-methylbenzofuran-3-carboxylic acid (206 mg, 1.0 mmol; Matrix) according to Method A. The resulting N-borane complex was deprotected according to Method D, and the product was purified by preparative HPLC (Waters XTerra® 5 μm 40×100 mm column, flow rate 40 mL/minute, 10-90% gradient over 25 minutes of acetonitrile in 0.1% aqueous trifluoroacetic acid, with UV detection at 254 nm) to afford the trifluoroacetate salt of the titled compound. $^1$H NMR (300 MHz, methanol-d$_4$) δ ppm 2.04 (s, 1 H), 2.09 (s, 1 H), 2.27 (s, 1 H), 2.39 (s, 1 H), 2.44 (s, 1 H), 2.56 (s, 2 H), 2.78 (s, 3 H), 3.61 (s, 2 H), 3.72 (s, 4 H), 3.84 (s, 3 H), 5.50 (t, J=3.2 Hz, 1 H), 6.93 (dd, J=9.0, 2.5 Hz, 1 H), 7.39 (d, J=9.2 Hz, 1 H), 7.46 (d, J=2.4 Hz, 1 H). MS (DCI/NH$_3$) m/z 342 (M+H)$^+$. Anal. Calcd. for C$_{20}$H$_{23}$NO$_4$.1.05C$_2$HF$_3$O$_2$: C, 57.56; H, 5.26; N, 3.04. Found: C, 57.56; H, 5.15; N, 3.02.

Example 47

(4s)-(Benzothien-5-ylcarbamoyloxy)-1-azatricyclo[3.3.1.1$^{3,7}$]decane

Example 47A (4s)-(Benzothien-5-ylcarbamoyloxy)-1-azatricyclo[3.3.1.1$^{3,7}$]decane N-borane Complex Prepared from the product of Example 36A (101 mg, 0.63 mmol) and benzothiophen-5-yl isocyanate (105 mg, 0.63 mmol; Acros) according to Method G. $^1$H NMR (300 MHz, methanol-d$_4$) δ ppm 1.69 (s, 1 H), 1.88 (d, J=11.8 Hz, 2 H), 2.03 (s, 2 H), 2.34 (d, J=12.5 Hz, 2H), 3.06-3.19 (m, 5 H), 3.26 (s, 1 H), 5.05 (s, 1 H), 7.28 (d, J=5.7 Hz, 1 H), 7.39 (dd, J=8.8, 2.0 Hz, 1 H), 7.54 (d, J=5.4 Hz, 1 H), 7.71-7.86 (m, 1 H), 8.00 (s, 1 H). MS (DCI/NH$_3$) m/z=329 (M+H)$^+$.

Example 47B (4s)-(Benzothien-5-ylcarbamoyloxy)-1-azatricyclo[3.3.1.1$^{3,7}$]decane Prepared as the p-toluenesulfonate salt from the product of Example 47A (180 mg, 0.599 mmol) according to Methods D and F. $^1$H NMR (300 MHz, methanol-d$_4$) δ ppm 1.95 (d, J=12.9 Hz, 2 H), 2.18 (s, 1 H), 2.27-2.58 (m, 7 H), 3.47-3.82

(m, 6 H), 5.15 (s, 1 H), 7.23 (d, J=7.8 Hz, 2 H), 7.29 (d, J=6.1 Hz, 1 H), 7.39 (d, J=10.5 Hz, 1 H), 7.56 (d, J=5.4 Hz, 1 H), 7.70 (d, J=8.1 Hz, 2 H), 7.80 (d, J=8.8 Hz, 1 H), 8.02 (s, 1 H). MS (DCI/NH$_3$) m/z=329 (M+H)$^+$. Anal. Calcd. for C$_{18}$H$_{20}$N$_2$O$_2$S.C$_7$H$_8$O$_3$S: C, 59.98; H, 5.64; N, 5.60. Found: C, 59.99; H, 5.56, H, 5.50.

Example 48

(4r)-(Benzothien-5-ylcarbamoyloxy)-1-azatricyclo [3.3.1.1$^{3,7}$]decane

Example 48A (4r)-(Benzothien-5-ylcarbamoyloxy)-1-azatricyclo [3.3.1.1$^{3,7}$]decane N-borane Complex Prepared from the product of Example 37A (100 mg, 0.63 mmol) and benzothiophen-5-yl isocyanate (104 mg, 0.63 mmol; Acros) according to Method G. $^1$H NMR (300 MHz, methanol-d$_4$) δ ppm 1.74 (s, 1 H), 1.89-2.09 (m, 4 H), 2.12-2.26 (m, 2 H), 3.01 (d, J=13.2 Hz, 2 H), 3.15 (m, 2 H), 3.48 (d, J=13.6 Hz, 2 H), 5.06 (s, 1 H), 7.29 (d, J=5.4 Hz, 1 H), 7.39 (dd, J=8.8, 2.0 Hz, 1 H), 7.55 (d, J=5.4 Hz, 1 H), 7.79 (d, J=8.5 Hz, 1 H), 8.01 (s, 1 H). MS (DCI/NH$_3$) m/z=329 (M+H)$^+$.

Example 48B (4r)-(Benzothien-5-ylcarbamoyloxy)-1-azatricyclo [3.3.1.1$^{3,7}$]decane Prepared as the p-toluenesulfonate salt from the product of Example 48A (178 mg, 0.599 mmol) according to Methods D and F. $^1$H NMR (300 MHz, chloroform-d) δ ppm 1.94-2.20 (m, 5 H), 2.25-2.40 (m, 5 H), 3.28 (d, J=12.9 Hz, 2 H), 3.46 (s, 2 H), 4.00 (d, J=13.2 Hz, 2H), 5.06 (s, 1 H), 7.18 (d, J=8.5 Hz, 2 H), 7.27 (s, 1 H), 7.37 (dd, J=8.6, 1.9 Hz, 1 H), 7.44 (d, J=5.4 Hz, 1 H), 7.76 (d, J=8.5 Hz, 1 H), 7.82 (d, J=8.5 Hz, 2 H), 8.01 (s, 1 H). MS (DCI/NH$_3$) m/z=329 (M+H)$^+$. Anal. Calcd. for C$_{18}$H$_{20}$N$_2$O$_2$S.C$_7$H$_8$O$_3$S: C, 59.98; H, 5.64; N, 5.60. Found: C, 59.93; H, 5.64, H, 5.39.

Example 49

(4s)-(4-Bromophenylcarbamoyloxy)-1-azatricyclo [3.3.1.1$^{3,7}$]decane

Example 49A (4s)-(4-Bromophenylcarbamoyloxy)-1-azatricyclo [3.3.1.1$^{3,7}$]decane N-borane Complex Prepared from the product of Example 36A (100 mg, 0.63 mmol) and 4-bromophenyl isocyanate (118 mg, 0.63 mmol; Aldrich) according to Method G. $^1$H NMR (300 MHz, chloroform-d) δ ppm 1.70 (d, J=12.2 Hz, 2 H), 2.00 (s, 1 H), 2.13 (d, J=12.9 Hz, 2 H), 2.21 (s, 2 H), 3.10-3.26 (m, 6 H), 5.02 (s, 1 H), 7.26-7.33 (m, 2 H), 7.38-7.49 (m, 2 H). MS (DCI/NH$_3$) m/z=363 (M+NH$_4$)$^+$.

Example 49B (4s)-(4-Bromophenylcarbamoyloxy)-1-azatricyclo [3.3.1.1$^{3,7}$]decane Prepared as the p-toluenesulfonate salt from the product of Example 49A (131 mg, 0.359 mmol) according to Methods D and F. $^1$H NMR (300 MHz, methanol-d$_4$) δ ppm 1.95 (d, J=12.9 Hz, 2 H), 2.18 (s, 1 H), 2.27-2.58 (m, 7 H), 3.47-3.82 (m, 6 H), 5.15 (s, 1 H), 7.23 (m, 4 H), 7.70 (m, 4 H). MS (DCI/NH$_3$) m/z=351 (M+H)$^+$. Anal. Calcd. for C$_{16}$H$_{19}$BrN$_2$O$_2$.C$_7$H$_8$O$_3$S: C, 52.78; H, 5.20; N, 5.35. Found: C, 52.23; H, 5.13, H, 5.20.

Example 50

(4r)-(4-Bromophenylcarbamoyloxy)-1-azatricyclo [3.3.1.1$^{3,7}$]decane

Example 50A (4r)-(4-Bromophenylcarbamoyloxy)-1-azatricyclo [3.3.1.1$^{3,7}$]decane N-borane Complex Prepared from the product of Example 37A (100 mg, 0.63 mmol) and 4-bromophenyl isocyanate (118 mg, 0.63 mmol; Aldrich) according to Method G. $^1$H NMR (300 MHz, chloroform-d) δ ppm 1.80 (s, 1 H), 1.92-2.06 (m, 4 H), 2.06-2.20 (m, 2 H), 3.05 (d, J=12.6 Hz, 2 H), 3.21 (d, 2 H), 3.54 (d, J=13.2 Hz, 2 H), 5.09 (s, 1 H), 7.28-7.37 (m, 2 H), 7.37-7.46 (m, 2H). MS (DCI/NH$_3$) m/z=363 (M+NH$_4$)$^+$.

Example 50B (4r)-(4-Bromophenylcarbamoyloxy)-1-azatricyclo [3.3.1.1$^{3,7}$]decane Prepared as the p-toluenesulfonate salt from the product of Example 50A (48 mg, 0.359 mmol) according to Methods D and F. $^1$H NMR (300 MHz, chloroform-d) δ ppm 1.94-2.20 (m, 5 H), 2.25-2.40 (m, 5 H), 3.28 (d, J=12.9 Hz, 2 H), 3.46 (s, 2 H), 4.00 (d, J=13.2 Hz, 2H), 5.06 (s, 1 H), 7.23 (m, 4 H), 7.70 (m, 4 H). MS (DCI/NH$_3$) m/z=351 (M+H)$^+$. Anal. Calcd. for C$_{16}$H$_{19}$BrN$_2$O$_2$.C$_7$H$_8$O$_3$S: C, 52.78; H, 5.20; N, 5.35. Found: C, 52.60; H, 5.23, H, 5.34.

Example 51

(4s)-(2-Hydroxyphenylcarbamoyloxy)-1-azatricyclo [3.3.1.1$^{3,7}$]decane

Example 51A (4s)-(Benzoxazol-2-yloxy)-1-azatricyclo[3.3.1.1$^{3,7}$]decane N-borane Complex A solution of Example 36A (103 mg, 0.616 mmol) and 2-chlorobenzoxazole (100 mg, 0.86 mmol; Aldrich) in anhydrous DMF (2 mL) was chilled to 0° C. and treated with sodium hydride (22 mg, 0.90 mmol; 95%, Aldrich). After 15 minutes, the cooling bath was removed and the reaction was allowed to stir overnight. The dark brown mixture was poured into water, stirred for 1 hour, and the resulting solid product was collected by filtration, washed with water and purified by flash chromatography (Analogix 34 g silica gel column, 5-95% gradient of ethyl acetate in hexanes) to afford the product. $^1$H NMR (300 MHz, chloroform-d) δ ppm 1.74 (d, J=12.2 Hz, 2 H), 2.06 (s, 1 H), 2.27 (d, J=12.9 Hz, 2 H), 2.50 (s, 2 H), 3.19-3.34 (m, 6 H), 5.29 (t, J=3.4 Hz, 1 H), 7.17-7.30 (m, 2 H), 7.35-7.40 (m, 1 H), 7.48 (dd, J=7.5, 1.7 Hz, 1 H).

Example 51B (4s)-(2-Hydroxyphenylcarbamoyloxy)-1-azatricyclo [3.3.1.1$^{3,7}$]decane Prepared from the product of Example 51A (141 mg, 0.496 mmol) according to Method D. $^1$H NMR (300 MHz, dimethylsulfoxide-d$_6$) δ ppm 1.51 (s, 1 H), 1.73 (d, J=11.9 Hz, 2 H), 1.82 (s, 2 H), 2.17 (d, J=11.9 Hz, 2 H), 2.88-2.99 (m, 4 H), 3.05-3.19 (m, 2 H), 4.89 (t, J=3.2 Hz, 1 H), 6.75 (td, J=7.5, 2.0

Hz, 1 H), 6.81-6.94 (m, 2 H), 7.59 (d, J=7.5 Hz, 1 H), 8.18 (s, 1 H), 9.70 (s, 1 H). MS (+ESI) m/z 289 (M+H)+.

Example 51C (4s)-(2-Hydroxyphenylcarbamoyloxy)-1-azatricyclo[3.3.1.1$^{3,7}$]decane Prepared as the p-toluenesulfonate salt from the product of Example 51B (64 mg, 0.22 mmol) and p-toluenesulfonic acid monohydrate (42 mg, 0.22 mmol; Aldrich) according to Method F. $^1$H NMR (300 MHz, methanol-d$_4$) δ ppm 1.92 (d, J=12.9 Hz, 2 H), 2.15 (s, 1 H), 2.28-2.46 (m, 7 H), 3.51-3.70 (m, 6 H), 5.12 (t, J=3.2 Hz, 1 H), 6.76-6.86 (m, 2 H), 6.89-6.98 (m, 1 H), 7.23 (d, J=7.8 Hz, 2 H), 7.67-7.74 (m, 2 H). MS (+ESI) m/z 289 (M+H)+. Anal. Calcd. for C$_{16}$H$_{20}$N$_2$O$_3$.C$_7$H$_8$O$_3$S.0.4H$_2$O: C, 59.06; H, 6.21; N, 5.99. Found: C, 58.84; H, 6.32; N, 5.86.

Example 52

(4s)-(2,3-Dihydrobenzofuran-5-ylcarbamoyloxy)-1-azatricyclo[3.3.1.1$^{3,7}$]decane Example 52A (4s)-(2,3-Dihydrobenzofuran-5-ylcarbamoyloxy)-1-azatricyclo[3.3.1.1$^{3,7}$]decane N-borane Complex Prepared from the product of Example 36A (100 mg, 0.63 mmol) and 2,3-dihydrobenzofuran-5-yl isocyanate (98 mg, 0.63 mmol; Acros) according to Method G. $^1$H NMR (300 MHz, methanol-d$_4$) δ ppm 1.86-2.41 (m, 7 H), 3.36-3.58 (m, 6 H), 3.68 (d, J=12.2 Hz, 2 H), 4.30 (s, 2 H), 4.93 (s, 1 H), 7.09-7.49 (m, 2 H), 7.97 (s, 1 H).

Example 52B (4s)-(2,3-Dihydrobenzofuran-5-ylcarbamoyloxy)-1-azatricyclo[3.3.1.1$^{3,7}$]decane Prepared as the p-toluenesulfonate salt from the product of Example 52A (35 mg, 0.10 mmol) according to Methods D and F. $^1$H NMR (300 MHz, methanol-d$_4$) δ ppm 1.95 (d, J=12.9 Hz, 2 H), 2.18 (s, 1 H), 2.27-2.58 (m, 7 H), 3.11-3.27 (m, 2 H), 3.47-3.82 (m, 6 H), 4.43-4.68 (m, 2 H), 5.15 (s, 1 H), 6.66-6.77 (m, 2 H), 6.96 (dd, J=8.5, 2.4 Hz, 1 H), 7.19 (d, J=7.8 Hz, 2 H), 7.79 (d, J=8.1 Hz, 2 H). MS (DCI/NH$_3$) m/z=351 (M+H)+.

Example 53

(4s)-(Benzylcarbamoyloxy)-1-azatricyclo[3.3.1.1$^{3,7}$]decane

Example 53A (4s)-(Benzylcarbamoyloxy)-1-azatricyclo[3.3.1.1$^{3,7}$]decane N-Complex Prepared from the product of Example 36A (100 mg, 0.62 mmol) and benzyl isocyanate (0.070 mL, 0.60 mmol) according to Method G. $^1$H NMR (300 MHz, chloroform-D) δ ppm 1.54 (s, 2 H), 1.65 (d, J=12.9 Hz, 2 H), 1.95 (s, 1 H), 2.01-2.21 (m, 3 H), 3.06-3.22 (m, 5 H), 4.38 (d, J=6.1 Hz, 2 H), 4.95 (s, 1 H), 7.27-7.39 (m, 5 H). MS (DCI/NH$_3$) m/z=287 (M+H)+.

Example 53B (4s)-(Benzylcarbamoyloxy)-1-azatricyclo[3.3.1.1$^{3,7}$]decane

Prepared as the p-toluenesulfonate salt from the product of Example 53A (105 mg, 0.35 mmol) according to Methods D and F. $^1$H NMR (300 MHz, methanol-d$_4$) δ ppm 1.95 (d, J=12.9 Hz, 2 H), 2.18 (s, 1 H), 2.27-2.58 (m, 5 H), 3.11-3.27 (m, 2 H), 3.47-3.82 (m, 3 H), 4.30 (s, 2 H), 4.43-4.68 (m, 2 H), 5.15 (s, 1 H), 7.24-7.43 (m, 5 H). MS (DCI/NH$_3$) m/z=287 (M+H)+.

Example 54

(4r)-(Benzylcarbamoyloxy)-1-azatricyclo[3.3.1.1$^{3,7}$]decane

Example 54A (4r)-(Benzylcarbamoyloxy)-1-azatricyclo[3.3.1.1$^{3,7}$]decane N-borane Complex Prepared from the product of Example 37A (100 mg, 0.62 mmol) and benzyl isocyanate (0.070 mL, 0.60 mmol) according to Method G. $^1$H NMR (300 MHz, chloroform-D) δ ppm 1.80 (s, 2 H), 1.92-2.06 (m, 4 H), 2.06-2.20 (m, 3 H), 3.05 (d, J=12.6 Hz, 2 H), 3.21 (d, 2 H), 3.54 (d, J=13.2 Hz, 2 H), 5.09 (s, 1 H), 7.27-7.39 (m, 5 H). MS (DCI/NH$_3$) m/z=287 (M+H)+.

Example 54B (4r)-(Benzylcarbamoyloxy)-1-azatricyclo[3.3.1.1$^{3,7}$]decane

Prepared as the p-toluenesulfonate salt from the product of Example 54A (180 mg, 0.60 mmol) according to Methods D and F. $^1$H NMR (300 MHz, chloroform-d) δ ppm 1.94-2.20 (m, 5 H), 2.25-2.40 (m, 4 H), 3.28 (d, J=12.9 Hz, 2 H), 3.46 (s, 2 H), 4.00 (d, J=13.2 Hz, 2H), 5.06 (s, 1 H), 7.15-7.43 (m, 5 H). MS (DCI/NH$_3$) m/z=287 (M+H)+.

Example 55

(4s)-1-Azatricyclo[3.3.1.1$^{3,7}$]dec-4-yl 5-(hexahydropyrrolo[3,4-c]pyrrol-2(1H)-yl)nicotinate Example 55A tert-Butyl 5-(5-ethoxycarbonylpyridin-3-yl)hexahydropyrrolo[3,4-c]pyrrole-2(1H)-carboxylate A suspension of tert-butyl hexahydropyrrolo[3,4-c]pyrrole-2(1H)-carboxylate (2.00 g, 9.42 mmol; see Schrimpf, Michael R.; Tietje, Karin R.; Toupence, Richard B.; Ji, Jianguo; Basha, Anwer; Bunnelle, William H.; Daanen, Jerome F.; Pace, Jennifer M.; Sippy, Kevin B. WO 2001081347), ethyl 5-bromonicotinate (2.80 g, 12.0 mmol; Aldrich), tris(dibenzylideneacetone)dipalladium(0) (259 mg, 0.283 mmol; Strem), 4,5-bis(diphenylphosphino)-9,9-dimethylxanthene (491 mg, 0.848 mmol; Aldrich) and cesium carbonate (4.91 g, 15.1 mmol; Aldrich) in anhydrous dioxane (50 mL) was heated at 90° C. for 72 hours. The reaction mixture was cooled and filtered through a glass frit. The filtrate was concentrated and the residue was purified by silica gel chromatography (50% ethyl acetate in hexane, R$_f$=0.15) to afford the title compound. MS (APCI) m/z=362 (M+H)+.

Example 55B 5-(5-(tert-Butoxycarbonyl)hexahydropyrrolo[3,4-c]pyrrol-2(1H)-yl)nicotinic Acid Example 55A (3.20 g, 8.90 mmol) was dissolved in a solvent mixture of ethanol (40 mL) and water (20 mL).

Sodium hydroxide (2 M, 13 mL) was added, and the reaction mixture was stirred at ambient temperature for 1 hour. The mixture was then diluted with ethyl acetate (100 mL) and was partitioned between ethyl acetate (250 mL) and water (30 mL). The aqueous layer was acidified to pH 4 and repartitioned between dichloromethane (200 mL) and water (250 mL). The organic layer was dried (sodium sulfate) and concentrated in vacuo to afford the title compound. $^1$H NMR (400 MHz, methanol-$d_4$) δ ppm 1.45 (s, 9 H), 3.06-3.14 (bs, 2 H), 3.27-3.34 (m, 4 H), 3.61 (dd, J=10.0, 7.5 Hz, 2 H), 3.64-3.71 (m, 2 H), 7.57 (dd, J=2.8, 1.8 Hz, 1 H), 8.04 (d, J=1.5 Hz, 1 H), 8.39 (s, 1 H). MS (APCI) m/z=334 (M+H)$^+$.

Example 55C (4s)-1-Azatricyclo[3.3.1.1$^{3,7}$]dec-4-yl-N-borane 5-(5-(tert-butoxycarbonyl)hexahydropyrrolo[3,4-c]pyrrol-2(1H)-yl)nicotinate Prepared from the product of Example 55B (110 mg, 0.33 mmol) and the product of Example 36A (67 mg, 0.40 mmol) according to Method B. MS (APCI) m/z=469 (M−BH$_3$+H)$^+$.

Example 55D (4s)-1-Azatricyclo[3.3.1.1$^{3,7}$]dec-4-yl 5-(hexahydropyrrolo[3,4-c]pyrrol-2(1H)-yl)nicotinate The product of Example 55C (110 mg, 0.23 mmol) was stirred in trifluoroacetic acid (5 mL) at ambient temperature for 1 hour. The mixture was concentrated and the residue was purified as described in Method D. The resulting solid was then dissolved in ether-methanol (5 mL, 10:1) and treated with fumaric acid (2 equivalents; 10 mg/mL solution in 10:1 ether-methanol). The precipitate was filtered and dried under vacuum to afford the fumarate of the title compound. $^1$H NMR (300 MHz, D$_2$O) δ ppm 1.87 (d, J=13.9 Hz, 2 H), 2.13-2.33 (m, 3 H), 2.46 (bs, 2 H), 3.13-3.34 (m, 4 H), 3.35-3.70 (m, 12 H), 5.37 (t, J=3.1 Hz, 1 H), 6.49 (s, 3 H; C$_4$H$_4$O$_4$), 7.71 (dd, J=1.7, 1.9 Hz, 1 H), 8.11 (bs, 1 H), 8.47 (s, 1 H). MS (DCI/NH$_3$) m/z=369 (M+H)$^+$. Anal. Calcd. for C$_{21}$H$_{28}$N$_4$O$_2$.2C$_4$H$_4$O$_4$.1.6H$_2$O: C, 55.34; H, 6.28; N, 8.90. Found: C, 55.11; H, 6.56; N, 8.89.

Example 56

(4r)-1-Azatricyclo[3.3.1.1$^{3,7}$]dec-4-yl 5-(hexahydropyrrolo[3,4-c]pyrrol-2(1H)-yl)nicotinate

Example 56A (4r)-1-Azatricyclo[3.3.1.1$^{3,7}$]dec-4-yl-N-borane 5-(5-(tert-butoxycarbonyl)hexahydropyrrolo[3,4-c]pyrrol-2(1H)-yl)nicotinate Prepared from the product of Example 55B (110 mg, 0.33 mmol) and the product of Example 37A (67 mg, 0.40 mmol) according to Method B. MS (APCI) m/z 469 (M−BH$_3$+H)$^+$.

Example 56B (4r)-1-Azatricyclo[3.3.1.1$^{3,7}$]dec-4-yl 5-(hexahydropyrrolo[3,4-c]pyrrol-2(1H)-yl)nicotinate Example 56A (138 mg, 0.29 mmol) was stirred in trifluoroacetic acid (5 mL) at ambient temperature for 1 hour. The mixture was concentrated and the residue was purified as described in Method D. The resulting solid was then dissolved in ether-MeOH (5 mL, 10:1) and treated with fumaric acid (2 equivalents; 10 mg/mL solution in 10:1 ether-MeOH). The precipitate was filtered and dried under vacuum to afford the fumarate salt of the title compound. $^1$H NMR (300 MHz, D$_2$O) δ ppm 2.05-2.15 (m, 2 H), 2.17-2.32 (m, 3 H), 2.54 (bs, 2 H), 3.26-3.41 (m, 4 H), 3.46-3.73 (m, 10 H), 3.77-3.88 (m, 2 H), 5.39 (t, J=3.4 Hz, 1 H), 6.64 (s, 3 H; C$_4$H$_4$O$_4$), 7.87 (dd, J=2.7, 1.7 Hz, 1 H), 8.20 (d, J=2.7 Hz, 1 H), 8.56 (d, J=1.4 Hz, 1 H). MS (ESI+) m/z=369 (M+H)$^+$. Anal. Calcd. for C$_{21}$H$_{28}$N$_4$O$_2$.2C$_4$H$_4$O$_4$.1 H$_2$O: C, 56.30; H, 6.19; N, 9.60. Found; C, 56.04; H, 6.26; N, 8.89.

Example 57

(4s)-1-Azatricyclo[3.3.1.1$^{3,7}$]dec-4-yl 2-bromothiazole-4-carboxylate

Example 57A 2-bromothiazole-4-carboxylic Acid

Ethyl 2-bromothiazole-4-carboxylate (600 mg, 2.54 mmol) was suspended in ethanol (15 mL). Sodium hydroxide (7.5 mL, 1 M) was added and the reaction mixture was stirred at 35° C. for 0.5 hours. The reaction mixture was acidified to pH ~3 with 1 M HCl, then diluted with water (100 mL) and extracted with ethyl acetate (2×50 mL). The organic extracts were combined, washed with brine (100 mL), dried (sodium sulfate), filtered and concentrated to provide the title compound. MS (APCI) m/z=208/210 (M+H)$^+$.

Example 57B (4s)-1-Azatricyclo[3.3.1.1$^{3,7}$]dec-4-yl 2-bromothiazole-4-carboxylate The product of Example 36A was processed as described in Method D to provide the deprotected free base, which then was converted to the hydrobromide salt using hydrobromic acid similarly to the procedure described in Method F. The salt was then coupled with the product of Example 57A according to Method B. The resulting mixture was concentrated and purified by preparative HPLC [Waters XTerra® RP18 column, 5 μm, 30×100 mm, flow rate 40 mL/minute, 5-95% gradient over 22 minutes of acetonitrile in buffer (0.1 M aqueous ammonium bicarbonate, adjusted to pH 10 with ammonium hydroxide)] to afford the desired product as its free base: $^1$H NMR (400 MHz, methanol-$d_4$) δ ppm 1.71 (br s, 1 H), 1.85-1.97 (m, 2 H), 2.06 (br s, 2 H), 2.28-2.46 (m, 2 H), 3.11-3.17 (m, 4 H), 3.25-3.29 (m, 2 H), 5.32 (t, J=3.1 Hz, 1H), 8.44 (s, 1 H). MS (ESI) m/z=343/345 (M+H)$^+$. Anal. Calcd. for C$_{13}$H$_{15}$BrN$_2$O$_2$S 0.25 H$_2$O: C, 44.9; H, 4.49; N, 8.06. Found: C, 44.73; H, 4.24; N, 8.27.

Example 58

(4s)-1-Azatricyclo[3.3.1.1$^{3,7}$]dec-4-yl 5-fluoronicotinate

The product of Example 36A (81 mg, 0.49 mmol) and 5-fluoronicotinic acid (82 mg, 0.58 mmol) were processed as described in Method B to provide the N-borane complex of the title compound. This intermediate was then deprotected as described in Method D and converted to the hydrochloride salt by the procedure of Method F: $^1$H NMR (500 MHz, methanol-$d_4$) δ ppm 1.92-2.07 (m, 2 H), 2.25 (br s, 1 H), 2.35-2.45 (m, 2 H), 2.53 (br s, 2 H), 3.60 (br s, 2 H), 3.64-3.77 (m, 4 H), 5.49 (t, J=3.4 Hz, 1 H), 8.21 (ddd, J=8.8, 2.8, 1.5 Hz, 1 H), 8.75 (d, J=2.7 Hz, 1 H), 9.07 (t, J=1.4 Hz, 1 H). MS (ESI) m/z=277 (M+H)$^+$. Anal. Calcd. for C$_{15}$H$_{17}$FN$_2$O$_2$.1.2 HCl: C, 56.29; H, 5.73; N, 8.75. Found: C, 56.6; H, 5.8; N, 8.83.

Example 59

(4s)-1-Azatricyclo[3.3.1.1$^{3,7}$]dec-4-yl 5-(1 H-pyrrol-1-yl)nicotinate

The product of Example 36A (83 mg, 0.49 mmol) and 5-(1 H-pyrrol-1-yl)nicotinic acid (93 mg, 0.49 mmol) were processed as described in Method B to provide the N-borane complex of the title compound. This intermediate was then deprotected as described in Method D and converted to the hydrochloride salt by the procedure of Method F: $^1$H NMR (400 MHz, methanol-d$_4$) δ ppm 1.98-2.09 (m, 2 H), 2.27 (br s, 1 H), 2.40-2.50 (m, 2 H), 2.58 (br s, 2 H), 3.62 (br s, 2 H), 3.67-3.80 (m, 4 H), 5.56 (br s, 1 H), 6.31-6.54 (m, 2 H), 7.39-7.61 (m, 2 H), 8.88 (dd, J=2.5, 1.5 Hz, 1 H), 9.17 (d, J=1.2 Hz, 1 H), 9.27 (d, J=2.5 Hz, 1 H). MS (DCI) m/z=324 (M+H)$^+$. Anal. Calcd. for C$_{19}$H$_{21}$NN$_3$O$_2$.1.55 HCl: C, 60.07; H, 5.98; N, 11.06. Found: C, 59.97; H, 5.91; N, 11.07.

Example 60

(4s)-1-Azatricyclo[3.3.1.1$^{3,7}$]dec-4-yl 3,4'-bipyridine-5-carboxylate

A solution of the (4s) isomer of Example 8A (85 mg, 0.24 mmol) in 2:1 isopropanol-water (2.4 mL) was reacted with pyridine-4-ylboronic acid (38.7 mg, 0.30 mmol) in the presence of sodium carbonate (64 mg, 0.59 mmol) and dichlorobis(triphenylphosphine)palladium (TI) (6.8 mg) at 93° C. for 1 hour. The reaction mixture was concentrated, and the residue was purified by preparative HPLC on a Waters Nova-Pak® HR C18 6 um 60 Å Prep-Pak cartridge column (40 mm×100 mm) using a gradient of 10% to 100% acetonitrile in 10 mM aqueous ammonium acetate over 12 minutes at a flow rate of 70 mL/minute to provide the N-borane complex of the title compound. It was then deprotected as described in Method D and converted to the hydrochloride salt by the procedure of Method F: $^1$H NMR (500 MHz, methanol-d$_4$) δ ppm 1.98-2.10 (m, 2 H), 2.27 (br s, 1 H), 2.41-2.53 (m, 2 H), 2.59 (br s, 2 H), 3.62 (br s, 2 H), 3.68-3.84 (m, 4 H), 5.58 (br s, 1 H), 8.62 (d, J=6.7 Hz, 2 H), 9.05 (d, J=6.4 Hz, 2 H), 9.14 (s, 1 H), 9.51 (br s, 2 H). MS (ESI) m/z=336 (M+H)$^+$.

Example 61

(4s)-1-Azatricyclo[3.3.1.1$^{3,7}$]dec-4-yl 5-(4-chlorophenyl)nicotinate

The (4s) isomer of Example 8A was coupled with 4-chlorophenylboronic acid as described in Method E to provide the N-borane complex of the title compound. This intermediate was then deprotected as described in Method D and converted to the hydrochloride salt by the procedure of Method F: $^1$H NMR (500 MHz, methanol-d$_4$) δ ppm 2.00-2.07 (m, 2H), 2.27 (br s, 1 H), 2.43-2.50 (m, 2 H), 2.59 (br s, 2 H), 3.62 (br s, 2 H), 3.67-3.87 (m, 4 H), 5.58 (br s, 1 H), 7.48-7.72 (m, 2 H), 7.77-7.97 (m, 2 H), 9.16 (t, J=2.0 Hz, 1 H), 9.35 (d, J=1.8 Hz, 1 H), 9.39 (d, J=1.5 Hz, 1 H). MS (ESI) m/z=369 (M+H)$^+$. Anal. Calcd. for C$_{21}$H$_{21}$ClN$_2$O$_2$.1.95 HCl$_2$.75H$_2$O: C, 51.53; H, 5.86; N, 5.72., Cl 21.37; Found; C, 51.53; H, 5.8; N, 5.71; Cl, 21.45.

Example 62

(4s)-1-Azatricyclo[3.3.1.1$^{3,7}$]dec-4-yl 5-(4-(trifluoromethyl)phenyl)nicotinate A solution of the (4s) isomer of Example 8A (81 mg, 0.23 mmol) in 10:1 toluene-water (6.6 mL) was coupled with 4-(trifluoromethyl)phenylboronic acid (57 mg, 0.30 mmol) in the presence of Na$_2$CO$_3$ (61 mg, 0.58 mmol) and dichlorobis (triphenylphosphine)palladium (II) (6.5 mg) at 105° C. for 20 minutes. The reaction mixture was concentrated and purified by flash chromatography on silica gel eluting with hexanes/ethyl acetate (1:1, R$_f$=0.4) to afford the N-borane complex of the title compound. The resulting material was then deprotected as described in Method D and converted to the hydrochloride salt by the procedure of Method F: $^1$H NMR (500 MHz, methanol-d$_4$) δ ppm 1.97-2.14 (m, 2 H), 2.27 (br s, 1 H), 2.40-2.52 (m, 2 H), 2.59 (br s, 2 H), 3.62 (br s, 2 H), 3.67-3.83 (m, 4 H), 5.58 (br s, 1 H), 7.91 (d, J=8.2 Hz, 2 H), 7.98-8.16 (m, 2 H), 9.14 (t, J=1.8 Hz, 1 H), 9.37 (d, J=1.5 Hz, 1 H), 9.42 (br s, 1 H). MS (DCI) m/z=403 (M+H)$^+$. Anal. Calcd. for C$_{22}$H$_{21}$F$_3$N$_2$O$_2$.1.9 HCl: C, 56.02; H, 4.89; N, 5.94. Found; C, 56.12; H, 4.77; N, 5.93.

Example 63

(4r)-1-Azatricyclo[3.3.1.1$^{3,7}$]dec-4-yl 5-(pyridin-2-yl)thiophene-2-carboxylate The title compound was prepared from the product of Example 1A and 5-(pyridin-2-yl)thiophene-2-carboxylic acid (Maybridge) according to Method A, and converted to the hydrochloride salt as described in Method C: $^1$H NMR (300 MHz, methanol-d$_4$) δ 1.99 (d, J=12.5 Hz, 2 H), 2.25 (s, 1 H), 2.38 (d, J=12.9 Hz, 2 H), 2.51 (s, 2 H), 3.60 (s, 2 H), 3.63-3.80 (m, 4 H), 5.46 (t, J=3.4 Hz, 1 H), 7.78-7.91 (m, 1 H), 7.86-8.11 (m, 2 H), 8.27-8.34 (m, 1 H), 8.39-8.52 (m, 1 H), 8.75 (d, J=6.4 Hz, 1 H). MS (DCI/NH$_3$) m/z 341 (M+H)$^+$.

Example 64

(4s)-1-Azatricyclo[3.3.1.1$^{3,7}$]dec-4-yl nicotinate

The product of Example 36A (89 mg, 0.53 mmol) and nicotinic acid (72 mg, 0.59 mmol) were processed as described in Method B to provide the N-borane complex of the title compound. This intermediate was then deprotected as described in Method D and converted to the hydrochloride salt by the procedure of Method F: $^1$H NMR (500 MHz, methanol-d$_4$) δ ppm 1.99-2.07 (m, 2 H), 2.26 (br s, 1 H), 2.41-2.48 (m, 2 H), 2.56 (br s, 2 H), 3.62 (br s, 2 H), 3.67-3.78 (m, 4 H), 5.57 (br s, 1 H), 8.22 (dd, J=7.9, 5.8 Hz, 1 H), 9.09 (d, J=4.9 Hz, 1 H), 9.14 (d, J=8.2 Hz, 1 H), 9.46 (s, 1 H). MS (ESI) m/z=259 (M+H)$^+$. Anal. Calcd. for C$_{15}$H$_{18}$N$_2$O$_2$.2.15 HCl: C, 53.51; H, 6.03; N, 8.32. Found: C, 53.42; H, 6.04; N, 8.25.

Determination of Biological Activity

To determine the effectiveness of representative compounds of this invention as ligands for α7 NNRs, the compounds of the invention were evaluated according to the [$^3$H]-DPPB binding assay. To determine the effectiveness of representative compounds of this invention as ligands for α4β2 NNRs, the compounds of the invention were evaluated according to the [$^3$H]-cytisine binding assay, which were performed as described below.

[$^3$H]-Cytisine Binding

Binding to α4β2 NNRs subtype was determined according to the conditions which were modified from the procedures described in Pabreza L. A., Dhawan, S., Kellar K. J., [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCU5 mM KC1/2 mM CaCl$_2$/2 mM MgCl$_2$/50 mM Tris-Cl, pH 7.4, 4° C.). Samples containing 100-200 μg of protein and 0.75 nM [$^3$H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 µL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(I+[Ligand]/K$_D$).

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 NNR subtype was determined using membrane enriched fractions from rat brain minus cerebellum or human cortex (ABS Inc., Wilmington, Del.) as described in Anderson, D. J.; Bunnelle, W.; Surber, B.; Du, J.; Surowy, C.; Tribollet, E.; Marguerat, A.; Bertrand, D.; Gopalakrishnan, M. J. Pharmacol. Exp. Ther. (2008), 324, 179-187 which is incorporated herein by reference. Briefly, pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). Seven log-dilution concentrations of test compounds containing 100-200 µg of protein, and 0.5 nM [$^3$H]-DPPB (62.8 Ci/mmol; R46V, Abbott Labs) were incubated in a final volume of 500 µL for 75 minutes at 4° C. in duplicate. Non-specific binding was determined in the presence of 10 µM methyllycaconitine. Bound radioactivity was collected on Millipore MultiScreen® harvest plates FB presoaked with 0.3% polyethyleneimine using a Packard cell harvester, washed with 2.5 mL ice-cold buffer, and radioactivity was determined using a Packard TopCount Microplate beta counter. IC$_{50}$ values were determined by nonlinear regression in Microsoft® Excel or Assay Explorer. K$_i$ values were calculated from the IC$_{50}$s using the Cheng-Prusoff equation, where K$_i$=IC$_{50}$/(1+[Ligand]/K$_D$). [$^3$H]-DPPB was obtained according to the preparation procedures described below.

[Methyl-$^3$H]2,2-Dimethyl-5-(6-phenyl-pyridazin-3-yl)-5-aza-2-azonia-bicyclo[2.2.1]heptane; Iodide Preparation

[Methyl-$^3$H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl (S,S)-5-(6-Phenyl-pyridazin-3-yl)-2,5-diaza-bicyclo[2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid. The filtrate was concentrated and the residue was purified by column chromatography on silica gel, eluting with ethyl acetate, to provide additional product: MS (DCI/NH$_3$) m/z 353 (M+H)$^+$.

Step 2: Preparation of (S,S)-2-Methyl 5-(6-phenyl-pyridazin-3-yl)-2,5-diaza-bicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with CH$_2$Cl$_2$—CH$_3$OH—NH$_4$OH (95:5:1) to provide the title compound: MS (DCI/NH$_3$) m/z 267 (M+H)$^+$.

Step 3: Preparation of [$^3$H]-(S,S)-2,2-Dimethyl-5-(6-phenyl-pyridazin-3-yl)-5-aza-2-azonia-bicyclo[2.2.1]heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 mL acetonitrile:water:trifluoroacetic acid (15:85:0.1). Approximately 0.9 mL per injection were made onto a Phenomenex® Luna® C18(2) column (5 micron, 250 mm×4.6 mm ID) using an Agilent HPLC system. [$^3$H]-DPPB was eluted by a gradient mobile phase from 10% B to 20% B in 20 minutes where Mobile Phase A=0.1% trifluoroacetic acid in water and Mobile Phase B=0.1% trifluoroacetic acid in acetonitrile at a flow rate of approximately 1 mL/minute. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 µL flow cell and a 3:1 ratio of Ultima-Flo M scintillation cocktail to HPLC mobile phase were used. The analyses were performed using a Phenomenex® Luna® C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/minute and the UV detection was set at 275 nm.

Compounds of the invention typically exhibited binding values (K$_i$) below 10 micromolar in one or both of these assays ([$^3$H]-Cytisine or [$^3$H]-DPPB binding). Preferred compounds had K$_i$ values ranging from 0.01 nanomolar to 100 nanomolar in one or both binding assays.

Compounds of the invention are ligands at α4β2, α7 NNRs, or both α4β2 and α7 NNRs that modulate function of α4β2, α7 NNRs, or both α4β2 and α7 NNRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α4β2, α7, or both α4β2 and α7 NNR receptor or agonists that activate the receptor. Binding to α412, α7, or both α412 and α7 receptors also trigger key signaling processes involving various kinases and phosphatases and protein-protein interactions that are important to effects on memory, cytoprotection, gene transcription and disease modification.

Compounds of the invention can exist in radiolabeled form containing one or more atoms having an atomic mass or mass number different from the atomic mass or mass number most abundantly found in nature. Radioisotopes of atoms such as hydrogen, carbon, phosphorous, sulfur, fluorine, chlorine, and iodine include, but are not limited to, $^3$H, $^{14}$C, $^{32}$P, $^{35}$S, $^{18}$F, $^{36}$Cl, and $^{125}$I, respectively. Compounds that contain other radioisotopes of these and/or other atoms are within the scope of this invention. Compounds containing tritium ($^3$H) and $^{14}$C radioisotopes are preferred in general for their case in preparation and detectability. Radiolabeled compounds of this invention can be prepared by the general methods well known to persons having ordinary skill in the art. Such radiolabeled compounds can be conveniently prepared by carrying out the procedures disclosed in the above Examples and Schemes by substituting a readily available radiolabeled reagent for a non-radiolabeled reagent. The radiolabeled compounds of the invention may be used as standards to determine the effectiveness of α7 NNR ligands in the binding assays described above.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I)

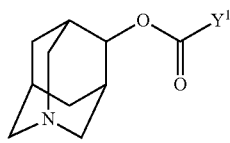

(I)

wherein
$Y^1$ is A, —N($R^X$)-A, or —C($R^Y$)=C($R^Z$)-A; with the proviso that $Y^1$ is other than unsubstituted benzothien-3-yl or 4-chlorophenyl;
A is an unsubstituted aryl, heteroaryl, unsubstituted arylalkyl, heteroarylalkyl, or heterocyclealkyl, wherein heteroaryl, the heteroaryl moiety of the heteroarylalkyl, and the heterocycle moiety of the heterocyclealkyl, are each independently unsubstituted or substituted; and
$R^X$, $R^Y$, and $R^Z$, at each occurrence, are each independently hydrogen, alkyl, or haloalkyl;
or a pharmaceutically acceptable salt, amide or ester thereof.
2. The compound of claim 1, wherein $Y^1$ is A, or a pharmaceutically acceptable salt, amide or ester thereof.
3. The compound of claim 2, wherein A is aryl or heteroaryl, or a pharmaceutically acceptable salt, amide or ester thereof.
4. The compound of claim 3, wherein the aryl or heteroaryl is substituted with at least one aryl, heteroaryl or heterocycle, or a pharmaceutically acceptable salt, amide, or ester thereof.
5. The compound of claim 1, wherein $Y^1$ is —N($R^X$)A, or a pharmaceutically acceptable salt, amide, or ester thereof.
6. The compound of claim 5, wherein A is aryl or heteroaryl, or a pharmaceutically acceptable salt, amide, or ester thereof.
7. The compound according to claim 5, wherein $R^X$ is hydrogen, or a pharmaceutically acceptable salt, amide, or ester thereof.
8. The compound of claim 5, wherein A is arylalkyl, or a pharmaceutically acceptable salt, amide, or ester thereof.
9. The compound according to claim 1, selected from the group consisting of
(4s)-(6-chloronicotinoyloxy)-1-azatricyclo[3.3.1.1.$^{3,7}$]decane;
(4r)-(6-chloronicotinoyloxy)-1-azatricyclo[3.3.1.1.$^{3,7}$]decane;
(4r)-(6-phenylnicotinoyloxy)-1-azatricyclo[3.3.1.1.$^{3,7}$]decane;
(4s)-[6-(indol-5-yl)nicotinoyloxy]-1-azatricyclo[3.3.1.1.$^{3,7}$]decane;
(4r)-[6-(indol-5-yl)nicotinoyloxy]-1-azatricyclo[3.3.1.1.$^{3,7}$]decane;
(4s)-(5-bromonicotinoyloxy)-1-azatricyclo[3.3.1.1.$^{3,7}$]decane;
(4r)-(5-bromonicotinoyloxy)-1-azatricyclo[3.3.1.1.$^{3,7}$]decane;
(4r)-(5-phenylnicotinoyloxy)-1-azatricyclo[3.3.1.1$^{3,7}$]decane;
(4s)-[5-(indol-5-yl)nicotinoyloxy]-1-azatricyclo[3.3.1.1$^{3,7}$]decane;
(4r)-[5-(indol-5-yl)nicotinoyloxy]-1-azatricyclo[3.3.1.1$^{3,7}$]decane;
(4s)-(furan-2-oyloxy)-1-azatricyclo[3.3.1.1$^{3,7}$]decane;
(4r)-(furan-2-oyloxy)-1-azatricyclo[3.3.1.1$^{3,7}$]decane;
(4s)-(5-bromofuran-2-oyloxy)-1-azatricyclo[3.3.1.1$^{3,7}$]decane;
(4r)-(5-bromofuran-2-oyloxy)-1-azatricyclo[3.3.1.1$^{3,7}$]decane;
(4s)-(4,5-dimethylfuran-2-oyloxy)-1-azatricyclo[3.3.1.1$^{3,7}$]decane;
(4r)-(4,5-dimethylfuran-2-oyloxy)-1-azatricyclo[3.3.1.1$^{3,7}$]decane;
(4s)-(thiophen-2-oyloxy)-1-azatricyclo[3.3.1.1$^{3,7}$]decane;
(4r)-(thiophen-2-oyloxy)-1-azatricyclo[3.3.1.1$^{3,7}$]decane;
(4s)-(thiophen-3-oyloxy)-1-azatricyclo[3.3.1.1$^{3,7}$]decane;
(4r)-(thiophen-3-oyloxy)-1-azatricyclo[3.3.1.1$^{3,7}$]decane;
(4s)-(5-chlorothiophen-2-oyloxy)-1-azatricyclo[3.3.1.1$^{3,7}$]decane;
(4r)-(5-chlorothiophen-2-oyloxy)-1-azatricyclo[3.3.1.1$^{3,7}$]decane;
(4s)-(5-methylthiophen-2-oyloxy)-1-azatricyclo[3.3.1.1$^{3,7}$]decane;
(4r)-(5-methylthiophen-2-oyloxy)-1-azatricyclo[3.3.1.1$^{3,7}$]decane;
(4s)-(5-bromothiophen-2-oyloxy)-1-azatricyclo[3.3.1.1$^{3,7}$]decane;
(4r)-(5-bromothiophen-2-oyloxy)-1-azatricyclo[3.3.1.1$^{3,7}$]decane;
(4s)-(3-bromothiophen-2-oyloxy)-1-azatricyclo[3.3.1.1$^{3,7}$]decane;

(4r)-(3-bromothiophen-2-oyloxy)-1-azatricyclo[3.3.1.1$^{3,7}$]decane;
(4s)-(5-(2-thienyl)thiophen-2-oyloxy)-1-azatricyclo[3.3.1.1$^{3,7}$]decane;
(4r)-(5-(2-thienyl)thiophen-2-oyloxy)-1-azatricyclo[3.3.1.1$^{3,7}$]decane;
(4s)-1-azatricyclo[3.3.1.1$^{3,7}$]decan-4-yl 2-(thiophen-2-yl)thiazole-4-carboxylate;
(4r)-1-azatricyclo[3.3.1.1$^{3,7}$]decan-4-yl 2-(thiophen-2-yl)thiazole-4-carboxylate;
(4s)-(2-naphthoyloxy)-1-azatricyclo[3.3.1.1$^{3,7}$]decane;
(4s)-(benzothiophen-5-oyloxy)-1-azatricyclo[3.3.1.1$^{3,7}$]decane;
(4r)-(benzothiophen-5-oyloxy)-1-azatricyclo[3.3.1.1$^{3,7}$]decane;
(4s)-(thieno[2,3-c]pyridine-5-oyloxy)-1-azatricyclo[3.3.1.1$^{3,7}$]decane;
(4r)-(thieno[2,3-c]pyridine-5-oyloxy)-1-azatricyclo[3.3.1.1$^{3,7}$]decane;
(4s)-(5-bromoindol-3-oyloxy)-1-azatricyclo[3.3.1.1$^{3,7}$]decane;
(4s)-(4-bromoindol-3-oyloxy)-1-azatricyclo[3.3.1.1$^{3,7}$]decane;
(4s)-(indol-3-oyloxy)-1-azatricyclo[3.3.1.1$^{3,7}$]decane;
(4s)-(indol-6-oyloxy)-1-azatricyclo[3.3.1.1$^{3,7}$]decane;
(4s)-(benzofuran-5-oyloxy)-1-azatricyclo[3.3.1.1$^{3,7}$]decane;
(4s)-(5-methoxy-2-methylbenzofuran-3-oyloxy)-1-azatricyclo[3.3.1.1$^{3,7}$]decane;
(4s)-(benzothien-5-ylcarbamoyloxy)-1-azatricyclo[3.3.1.1$^{3,7}$]decane;
(4r)-(benzothien-5-ylcarbamoyloxy)-1-azatricyclo[3.3.1.1$^{3,7}$]decane;
(4s)-(4-bromophenylcarbamoyloxy)-1-azatricyclo[3.3.1.1$^{3,7}$]decane;
(4r)-(4-bromophenylcarbamoyloxy)-1-azatricyclo[3.3.1.1$^{3,7}$]decane;
(4s)-(2-hydroxyphenylcarbamoyloxy)-1-azatricyclo[3.3.1.1$^{3,7}$]decane;
(4s)-(benzylcarbamoyloxy)-1-azatricyclo[3.3.1.1$^{3,7}$]decane;
(4r)-(benzylcarbamoyloxy)-1-azatricyclo[3.3.1.1$^{3,7}$]decane;
(4s)-1-azatricyclo[3.3.1.1$^{3,7}$]dec-4-yl 5-(hexahydropyrrolo[3,4-c]pyrrol-2(1H)-yl)nicotinate;
(4r)-1-azatricyclo[3.3.1.1$^{3,7}$]dec-4-yl 5-(hexahydropyrrolo[3,4-c]pyrrol-2(1H)-yl)nicotinate;
(4s)-1-azatricyclo[3.3.1.1$^{3,7}$]dec-4-yl 2-bromothiazole-4-carboxylate;
(4s)-1-azatricyclo[3.3.1.1$^{3,7}$]dec-4-yl 5-fluoronicotinate;
(4s)-1-azatricyclo[3.3.1.1$^{3,7}$]dec-4-yl 5-(1H-pyrrol-1-yl)nicotinate;
(4s)-1-azatricyclo[3.3.1.1$^{3,7}$]dec-4-yl 3,4'-bipyridine-5-carboxylate;
(4s)-1-azatricyclo[3.3.1.1$^{3,7}$]dec-4-yl 5-(4-chlorophenyl)nicotinate;
(4s)-1-azatricyclo[3.3.1.1$^{3,7}$]dec-4-yl 5-(4-(trifluoromethyl)phenyl)nicotinate;
(4r)-1-azatricyclo[3.3.1.1$^{3,7}$]dec-4-yl 5-(pyridin-2-yl)thiophene-2-carboxylate; and
(4s)-1-azatricyclo[3.3.1.1$^{3,7}$]dec-4-yl nicotinate;
or a pharmaceutically acceptable salt, amide or ester thereof.

10. The compound according to claim 1, selected from the group consisting of
(4s)-(2-naphthoyloxy)-1-azatricyclo[3.3.1.1$^{3,7}$]decane;
(4s)-(benzothiophen-5-oyloxy)-1-azatricyclo[3.3.1.1$^{3,7}$]decane;
(4s)-(indol-3-oyloxy)-1-azatricyclo[3.3.1.1$^{3,7}$]decane;
(4s)-(indol-6-oyloxy)-1-azatricyclo[3.3.1.1$^{3,7}$]decane;
(4s)-(benzofuran-5-oyloxy)-1-azatricyclo[3.3.1.1$^{3,7}$]decane;
or pharmaceutically acceptable salts, amides or esters thereof.

11. A pharmaceutical composition comprising a therapeutically effective amount of the compound of claim 1, or a pharmaceutically acceptable salt, amide or ester thereof, in combination with one or more pharmaceutically acceptable carriers.

12. The pharmaceutical composition of claim 11, further comprising one or more atypical antipsychotics.

* * * * *